US011154346B2

(12) United States Patent
Boudreaux

(10) Patent No.: US 11,154,346 B2
(45) Date of Patent: Oct. 26, 2021

(54) FIRING AND LOCKOUT ASSEMBLY FOR KNIFE FOR ELECTROSURGICAL SHEARS

(71) Applicant: ETHICON LLC, Guaynabo, PR (US)

(72) Inventor: Chad P. Boudreaux, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 325 days.

(21) Appl. No.: 15/989,448

(22) Filed: May 25, 2018

(65) Prior Publication Data
US 2019/0357966 A1     Nov. 28, 2019

(51) Int. Cl.
| A61B 18/14 | (2006.01) |
| A61B 90/00 | (2016.01) |
| A61B 17/00 | (2006.01) |
| A61B 18/00 | (2006.01) |
| A61B 18/12 | (2006.01) |

(52) U.S. Cl.
CPC ...... *A61B 18/1442* (2013.01); *A61B 2017/00407* (2013.01); *A61B 2018/0063* (2013.01); *A61B 2018/00589* (2013.01); *A61B 2018/00607* (2013.01); *A61B 2018/126* (2013.01); *A61B 2018/1455* (2013.01); *A61B 2090/035* (2016.02); *A61B 2090/0811* (2016.02)

(58) Field of Classification Search
CPC ...... A61B 18/1442; A61B 2017/00407; A61B 2017/2945; A61B 2018/00196; A61B 2018/00202; A61B 2018/00589; A61B 2018/00607; A61B 2018/0063; A61B 2018/00916; A61B 2018/126; A61B 2018/1455; A61B 2090/0811; A61B 2090/035

USPC ........................................................ 606/45–52
See application file for complete search history.

(56) References Cited

U.S. PATENT DOCUMENTS

| 6,500,176 | B1 | 12/2002 | Truckai et al. |
| 7,112,201 | B2 | 9/2006 | Truckai et al. |
| 7,125,409 | B2 | 10/2006 | Truckai et al. |
| 7,131,970 | B2 * | 11/2006 | Moses ............... A61B 18/1442 606/51 |

(Continued)

OTHER PUBLICATIONS

U.S. Appl. No. 15/989,424, entitled "Method and Apparatus for Open Electrostusical Shears," filed May 25, 2018.

(Continued)

*Primary Examiner* — Michael F Peffley
(74) *Attorney, Agent, or Firm* — Frost Brown Todd LLC

(57) ABSTRACT

A surgical instrument includes an end effector, a handle assembly, and a knife drive assembly. The end effector includes a first jaw, a second jaw, a knife, and an electrode assembly. The handle assembly includes a housing, and an arm. The arm may pivot the second jaw between the open position and the closed position. The knife drive assembly includes an input assembly, and output assembly coupled with the knife, and a compound pulley assembly. The compound pulley assembly includes a pair of pulley wheels each having an input track, an output track, an input cable, and an output cable. The input assembly can drive the input cable a first proximal distance in order to rotate the pair of pulley wheels in a first angular direction, thereby driving the output cable a first distal direction to actuate the knife from the pre-fired position toward the fired position.

20 Claims, 24 Drawing Sheets

(56) References Cited

U.S. PATENT DOCUMENTS

| | | |
|---|---|---|
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 8,939,974 B2 | 1/2015 | Boudreaux et al. |
| 9,089,327 B2 | 7/2015 | Worrell et al. |
| 9,161,803 B2 | 10/2015 | Yates et al. |
| 9,402,682 B2 | 8/2016 | Worrell et al. |
| 9,545,253 B2 | 1/2017 | Worrell et al. |
| 9,610,114 B2 | 4/2017 | Baxter, III et al. |
| 9,877,720 B2 | 1/2018 | Worrell et al. |
| 10,111,699 B2 | 10/2018 | Boudreaux |
| 10,772,642 B2 | 9/2020 | Kappus et al. |
| 2009/0149854 A1* | 6/2009 | Cunningham ..... A61B 18/1442 606/51 |
| 2011/0218530 A1* | 9/2011 | Reschke ................ A61B 18/18 606/52 |
| 2011/0257680 A1* | 10/2011 | Reschke ............. A61B 17/285 606/206 |
| 2011/0276049 A1* | 11/2011 | Gerhardt ........... A61B 18/1402 606/45 |

OTHER PUBLICATIONS

U.S. Appl. No. 15/989,430, entitled "Electrosurgical Shears with Knife Lock and Clamp-Actuated Switch," filed May 25, 2018.

U.S. Appl. No. 15/989,433, entitled "Knife Drive Assembly for Electrosurgical Shears," filed May 25, 2018.

U.S. Appl. No. 15/989,438, entitled "Knife Auto-Return Assembly for Electrosurgical Shears," filed May 25, 2018.

U.S. Appl. No. 15/989,442, entitled "Compound Screw Knife Drive for Electrosurgical Shears," filed May 25, 2018.

U.S. Appl. No. 15/989,452, entitled "Dual Stage Energy Activation for Electrosurgical Shears," filed May 25, 2018.

U.S. Appl. No. 15/989,455, entitled "Latching Clamp Arm for Electrosurgical Shears," filed May 25, 2018.

International Search Report and Written Opinion dated Oct. 28, 2019 for Application No. PCT/IB2019/053694, 15 pgs.

* cited by examiner

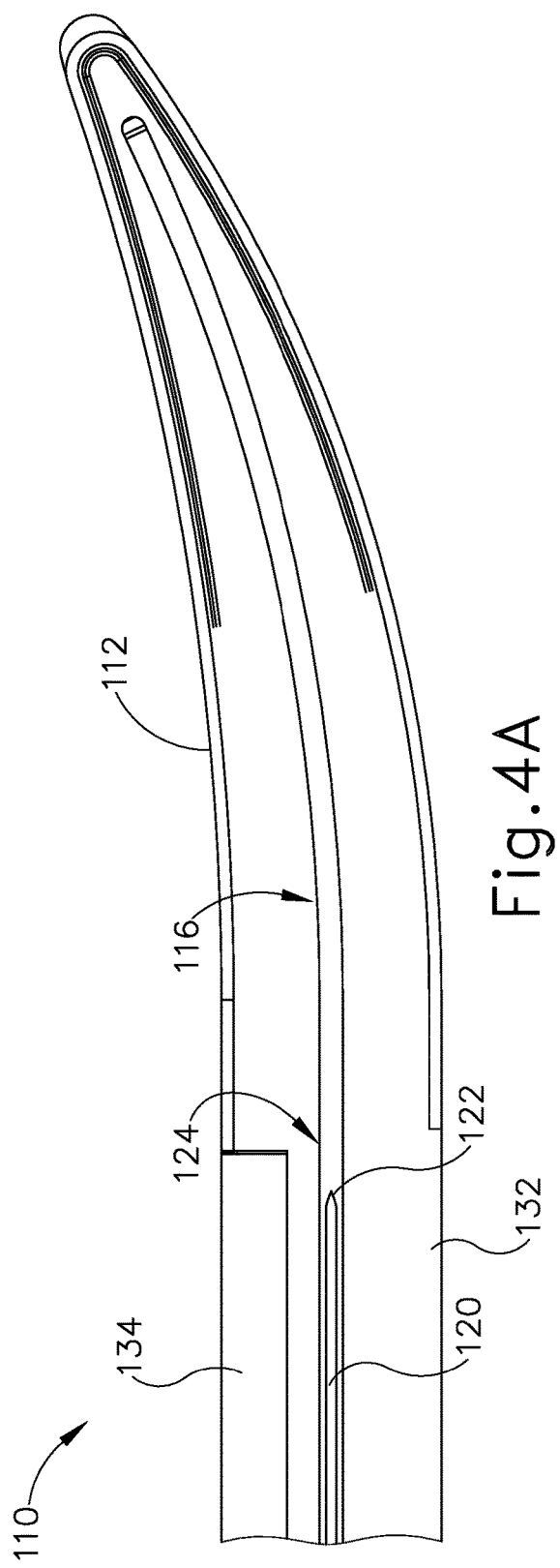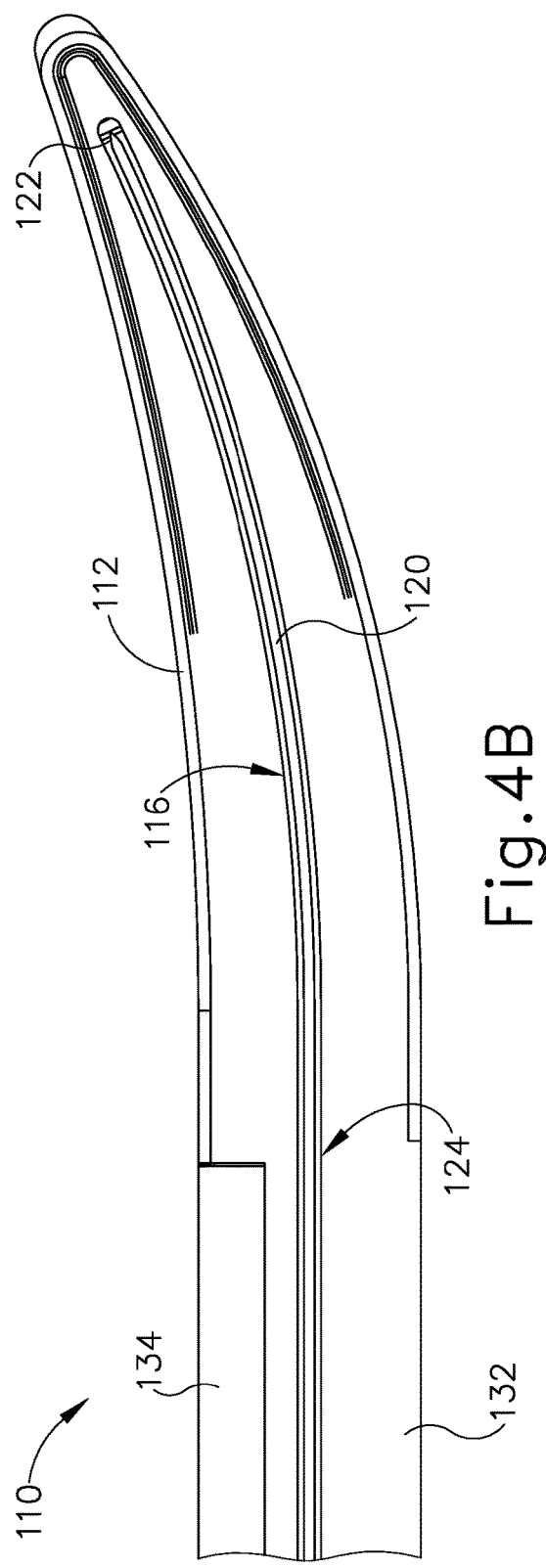

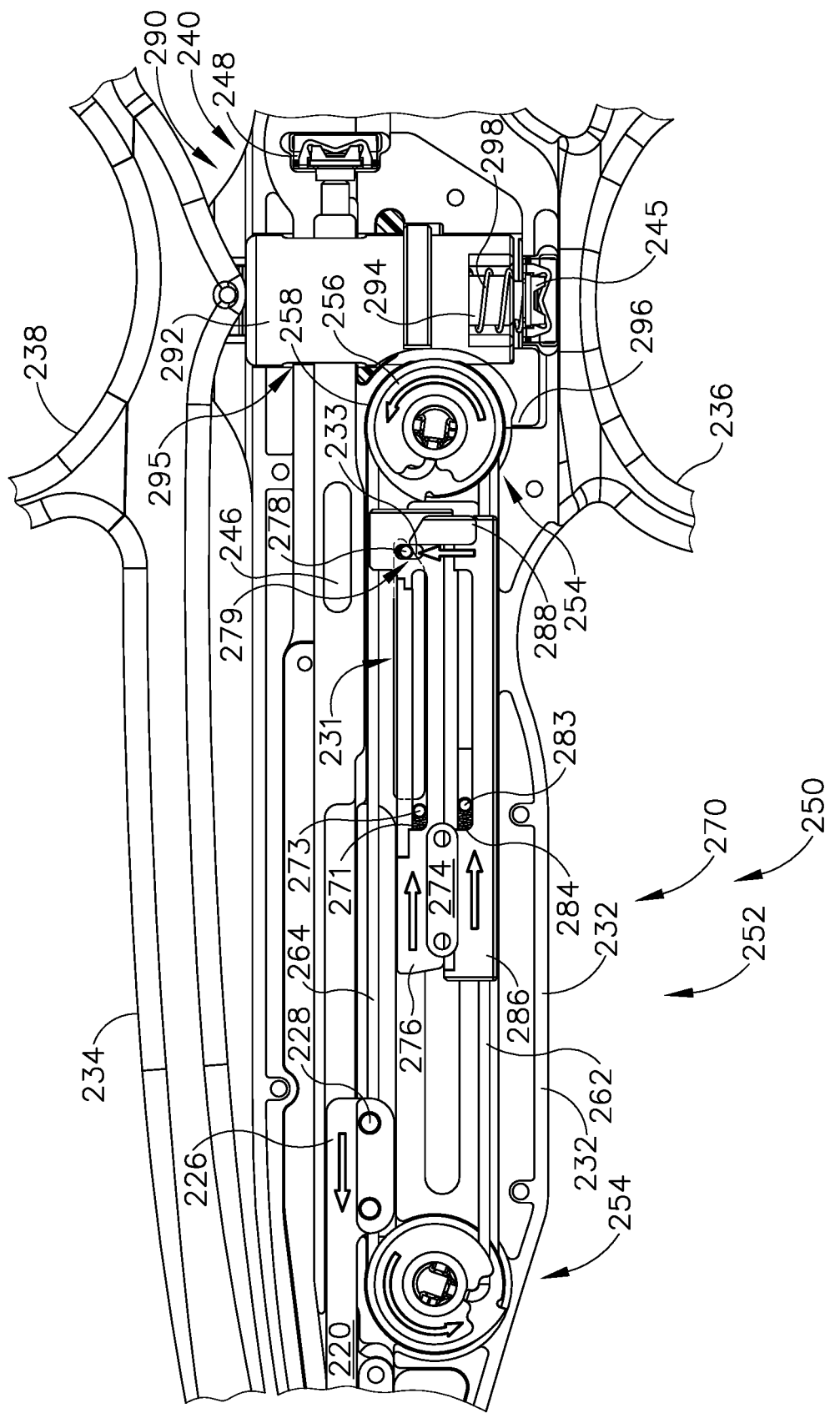

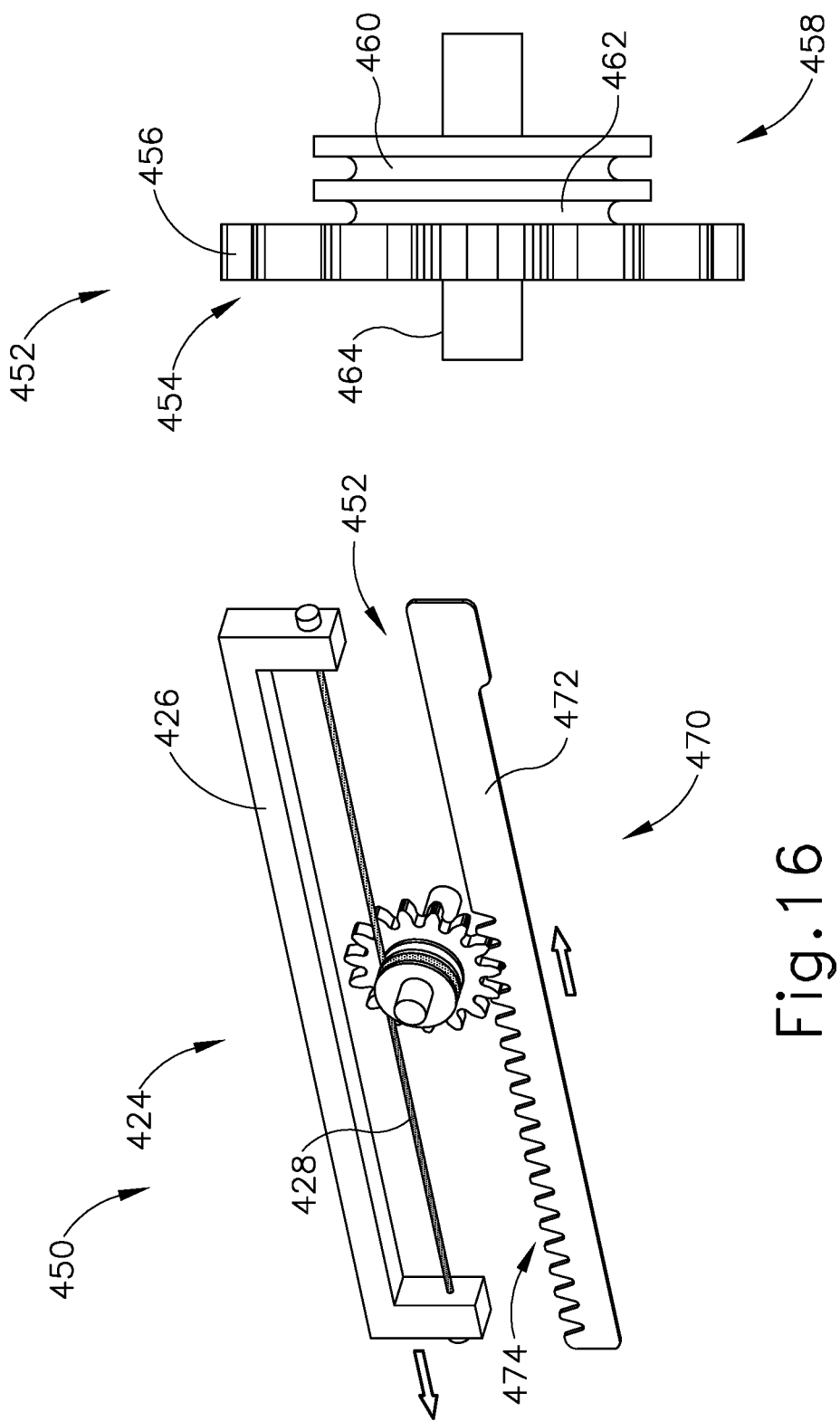

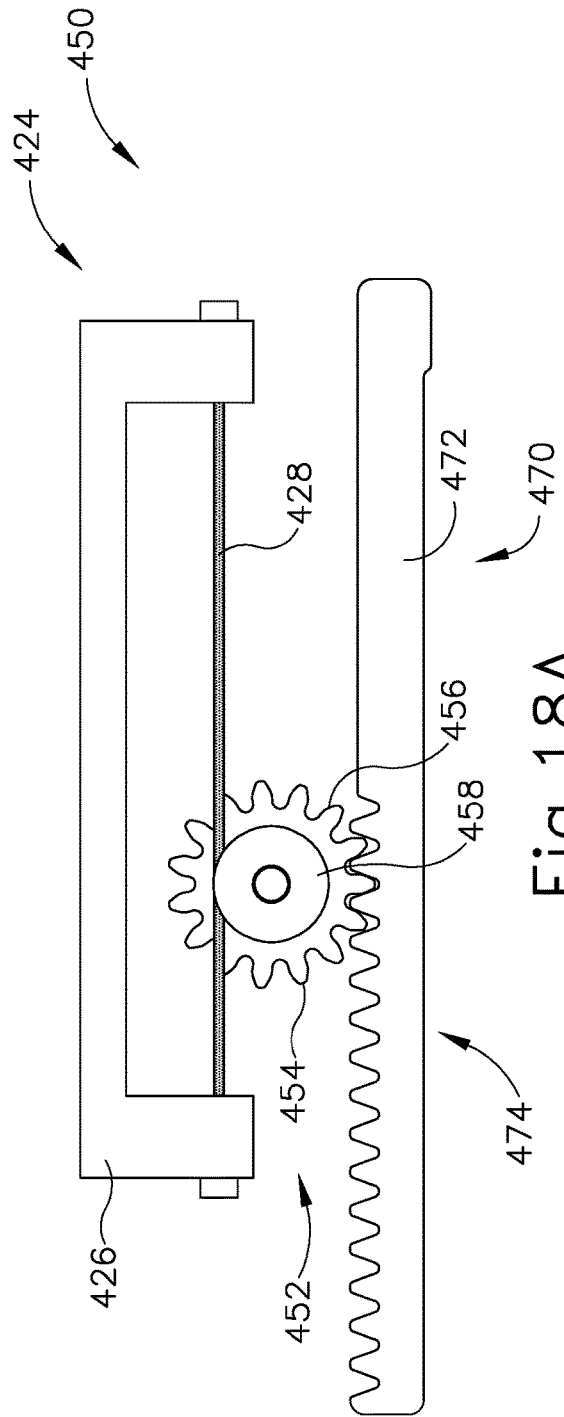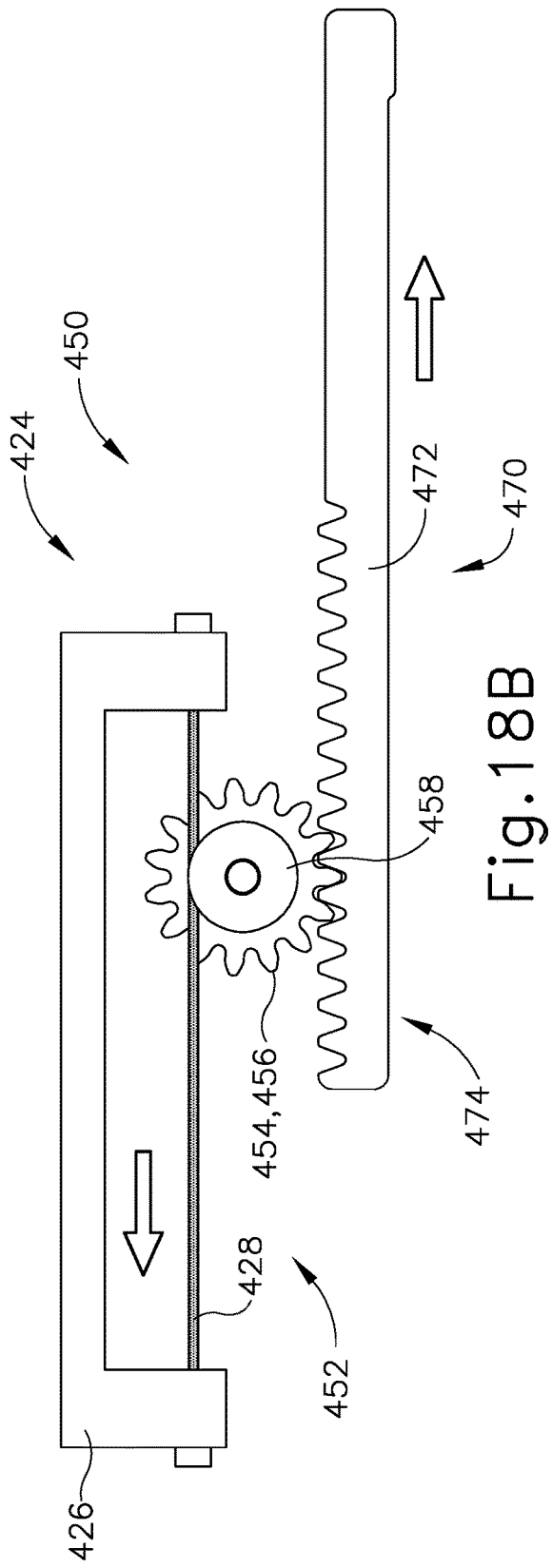

FIRING AND LOCKOUT ASSEMBLY FOR KNIFE FOR ELECTROSURGICAL SHEARS

BACKGROUND

A variety of surgical instruments include one or more elements that transmit RF energy to tissue (e.g., to coagulate or seal the tissue). Some such instruments comprise a pair of jaws that open and close on tissue, with conductive tissue contact surfaces that are operable to weld tissue clamped between the jaws. In open surgical settings, some such instruments may be in the form of forceps having a scissor grip.

In addition to having RF energy transmission elements, some surgical instruments also include a translating tissue cutting element. An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pat. No. 8,939,974, entitled "Surgical Instrument Comprising First and Second Drive Systems Actuatable by a Common Trigger Mechanism," issued Jan. 27, 2015, the disclosure of which is incorporated by reference herein; U.S. Pat. No. 9,161,803, entitled "Motor Driven Electrosurgical Device with Mechanical and Electrical Feedback," issued Oct. 20, 2015, the disclosure of which is incorporated by reference herein; U.S. Pat. No. 9,877,720, entitled "Control Features for Articulating Surgical Device," issued Jan. 30, 2018, the disclosure of which is incorporated by reference herein; U.S. Pat. No. 9,402,682, entitled "Articulation Joint Features for Articulating Surgical Device," issued Aug. 2, 2016, the disclosure of which is incorporated by reference herein; U.S. Pat. No. 9,089,327, entitled "Surgical Instrument with Multi-Phase Trigger Bias," issued Jul. 28, 2015, the disclosure of which is incorporated by reference herein; and U.S. Pat. No. 9,545,253, entitled "Surgical Instrument with Contained Dual Helix Actuator Assembly," issued Jan. 17, 2017, the disclosure of which is incorporated by reference herein.

Some versions of electrosurgical instruments that are operable to sever tissue may be selectively used in at least two modes. One such mode may include both severing tissue and coagulating tissue. Another such mode may include just coagulating tissue without also severing the tissue. Yet another mode may include the use of jaws to grasp and manipulate tissue without also coagulating and/or severing the tissue. When an instrument includes grasping jaws and tissue severing capabilities, the instrument may also include a feature that ensures full closure of the jaws before the tissue is severed and/or before the electrodes are activated.

While various kinds of surgical instrument have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 4A depicts a cross-sectional view of the end effector of FIG. 1, taken along line 4-4 of FIG. 1, where the translating knife of FIG. 2 is in the proximal position;

FIG. 4B depicts a cross-sectional view of the end effector of FIG. 1, taken along line 4-4 of FIG. 1, where the translating knife of FIG. 2 is in the distal position;

FIG. 15D depicts a side elevational view of a portion of the instrument of FIG. 5, with a portion of the handle assembly of FIG. 7 omitted for clarity, where the end effector is in the closed position, where the resilient arm is in the flexed position, where the lockout assembly of FIG. 8 is in the unlocked configuration, and where the firing assembly of FIG. 9 is in a second fired position;

FIG. 16 depicts a perspective view of an alternative firing assembly that may be readily incorporated into the instrument of FIG. 5;

FIG. 17 depicts a top plan view of rotary drive assembly of the firing assembly of FIG. 16;

FIG. 18A depicts a side elevational view of the firing assembly of FIG. 16 in a pre-fired position; and FIG. 18B depicts a side elevational view of the firing assembly of FIG. 16 in a fired position.

Figure 1:
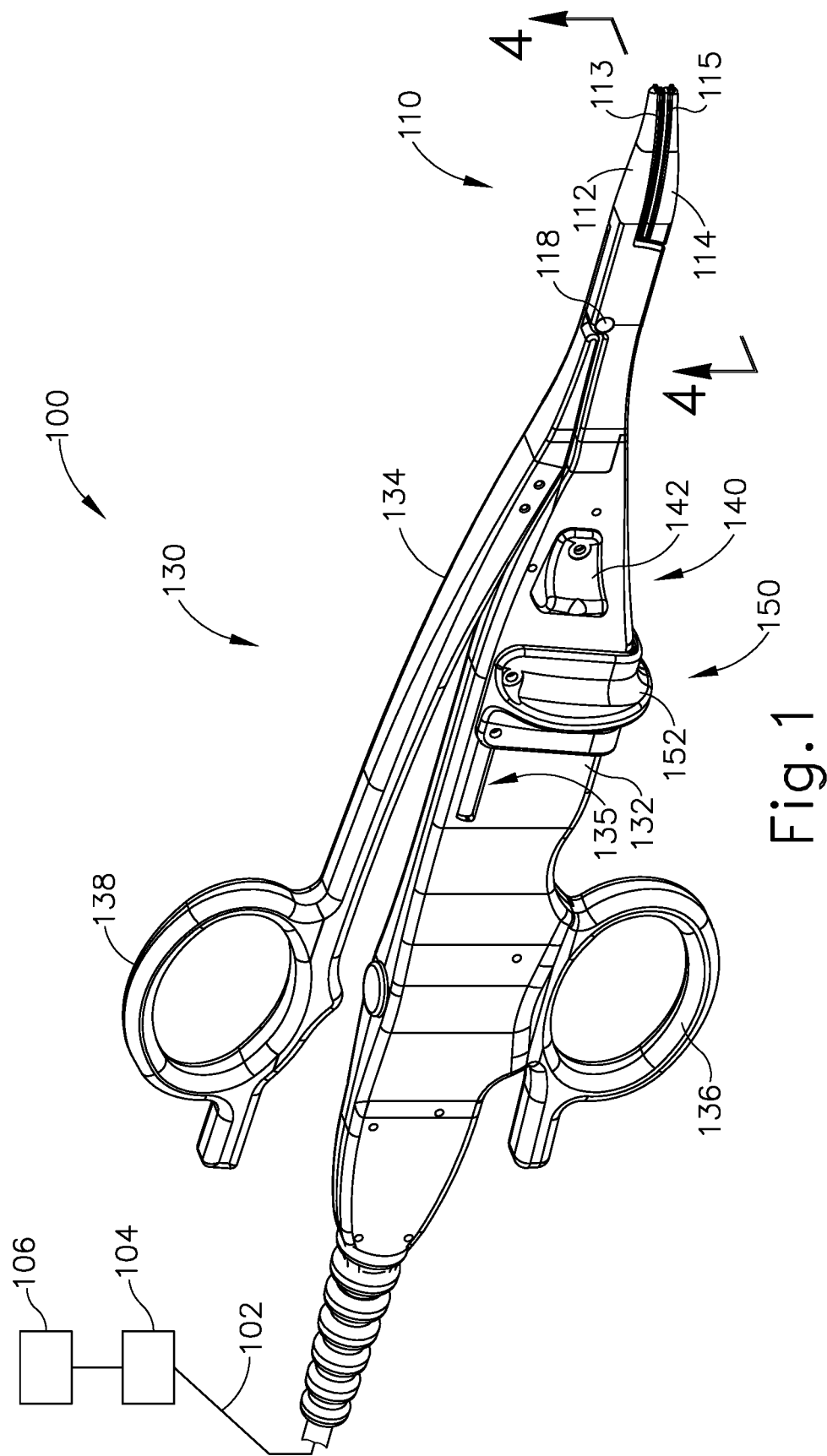
FIG. 1 depicts a perspective view of an exemplary electrosurgical forceps instrument, where an end effector is in a closed position, where a resilient arm is in a relaxed position.
Figure 2:
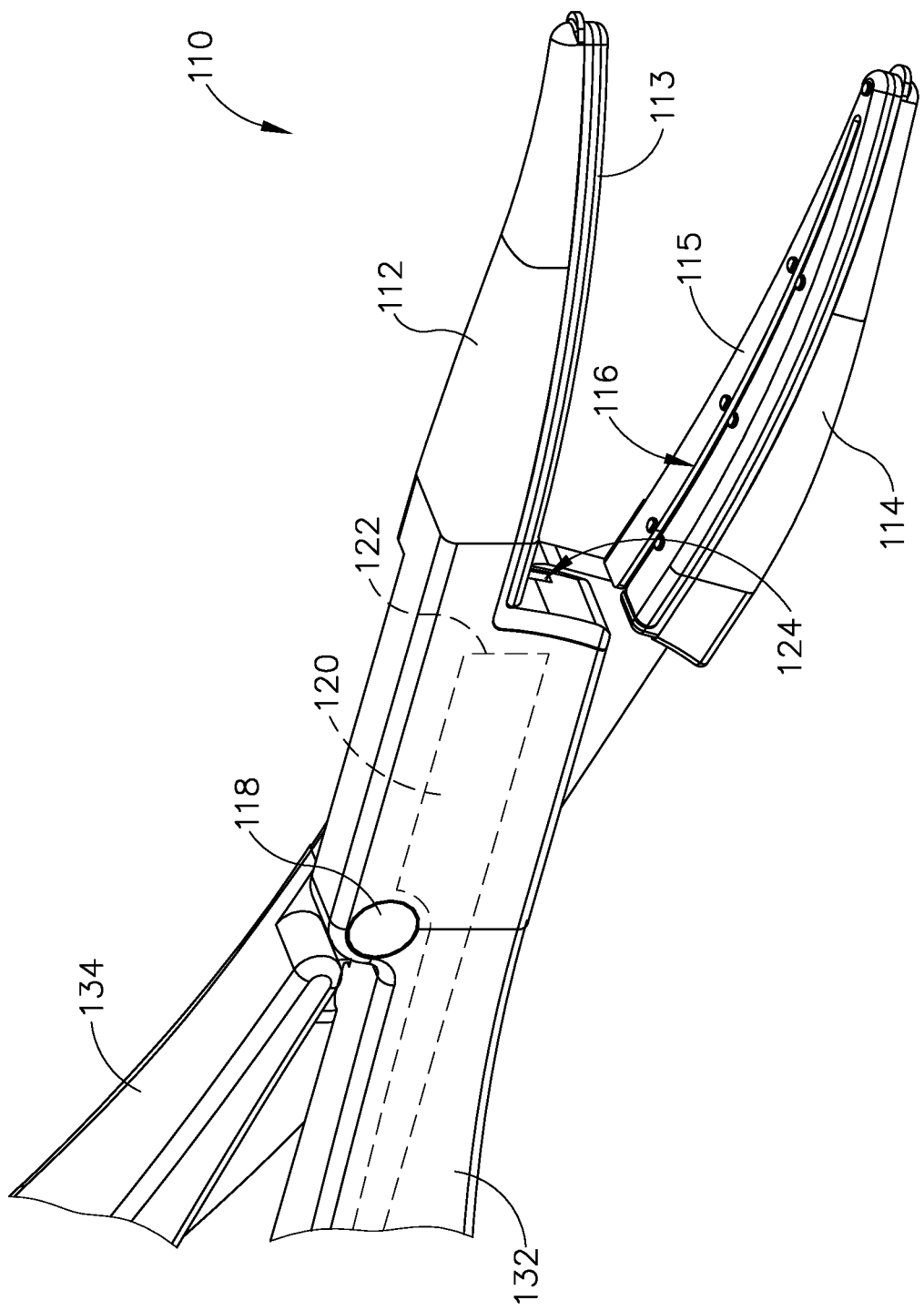
FIG. 2 depicts a perspective view of the end effector of FIG. 1 in an opened position, where a translating knife is in a proximal position.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Electrosurgical Forceps

As previously noted, an electrosurgical instrument may include a set of jaws, with at least one of the jaws being pivotable relative to the other jaw to selectively compress tissue between the jaws. Once the tissue is compressed, electrodes in the jaws may be activated with bipolar RF energy to seal the tissue. In some instances, a cutting feature is operable to sever tissue that is clamped between the jaws. For instance, the cutting feature may be actuated before or after the RF energy has sealed the tissue. Various references that are cited herein relate to electrosurgical instruments where the jaws are part of an end effector at the distal end of an elongate shaft, such that the end effector and the shaft may be inserted through a port (e.g., a trocar) to reach a site within a patient during a minimally invasive endoscopic surgical procedure. A handle assembly may be positioned at the proximal end of the shaft for manipulating the end effector. Such a handle assembly may have a pistol grip configuration or some other configuration.

In some instances, it may be desirable to provide an electrosurgical instrument that does not have an elongate shaft or handle assembly similar to those described in the various references cited herein. In particular, it may be desirable to provide an electrosurgical instrument that is configured similar to a forceps device, with a scissor grip. Such instruments may be used in a variety of medical procedures. Various examples of electrosurgical shears/forceps devices are disclosed in U.S. Pat. No. 9,610,144, entitled "Electrosurgical Hand Shears," filed Jan. 29, 2013, the disclosure of which is incorporated by reference herein. Various other examples of electrosurgical forceps instruments will be described in greater detail below; while other examples will be apparent to those of ordinary skill in the art in view of the teachings herein.

FIGS. 1-4B show an exemplary electrosurgical forceps instrument (100).

Instrument (100) includes a handle assembly (130) extending distally into an end effector (110). As will be described in greater detail below, instrument (100) may be used to grasp, seal, and sever tissue captured by end effector (110).

End effector (110) includes a first jaw (112) having a first electrode (113), a second jaw (114) having a second electrode (115), and a knife (120) configured to translate through the first jaw (112) and the second jaw (114). First jaw (112) and second jaw (114) are pivotably coupled with each other via pivot pin (118). First jaw (112) and second jaw (114) may pivot between an open position (FIG. 2) and a closed position (FIG. 1) in order to grasp tissue. First and second electrodes (113, 115) are positioned on respective jaws (112, 114) such that electrodes (113, 115) face each other when jaws (112, 114) are pivoted into the closed position. Additionally, each electrode (113, 115) is U-shaped in the present example, with the bend of the U-shape located near the distal end of each respective jaw (112, 114), such that each electrode (113, 115) includes two longitudinally extending, laterally spaced-apart legs extending along the length of each respective jaw (112, 114). Laterally spaced-apart legs of each electrode (113, 115) and corresponding portions of jaws (112, 114) define an elongate slot (116). Elongate slot (116) is dimensioned to slidably receive knife (120) such that knife may translate from a proximal position (FIG. 4A) to a distal position (FIG. 4B). Knife (120) includes a distal cutting edge (122) configured to sever tissue captured between jaws (112, 114) in the closed position.

A cable (102) extends proximally from handle assembly (130). Cable (102) is coupled with a control unit (104), which is further coupled with a power source (106). Power source (106) may power control unit (104). Control unit (104) is operable to provide RF power to electrodes (113, 115) of jaws (112, 114), to thereby seal tissue suitably captured between jaws (112, 114).

Handle assembly (130) includes a housing (132), and a resilient arm (134).

Housing (132) contains an electrode activation assembly (140) and a firing assembly (150). Housing (132) and resilient arm (134) are pivotably coupled with each other via pivot pin (118). Housing (132) extends distally into first jaw (112), while resilient arm (134) extends distally into second jaw (114). Housing (132) defines a knife pathway (124) that slidably houses knife (120). Housing (132) includes a finger ring (136) while resilient arm (134) terminates proximally into a thumb ring (138). Therefore, the operator may grasp instrument (100) in a scissor grip fashion and pivot resilient arm (134) relative to housing (132) via rings (136, 138) in order to open and close jaws (112, 114).

Resilient arm (134) is sufficiently resilient that arm (134) may flex from a relaxed position (FIG. 3B) to a flexed position (FIG. 3C) in response to pivoting arm (134) further toward housing (132) when jaws (112, 114) are already in the closed position. Resilient arm (134) is biased toward the relaxed position. Further pivoting of resilient arm (134) into the flexed position may result in greater closure forces between jaws (112, 114) as compared to pivoting jaws (112, 114) into the closed position while arm (134) is in the relaxed position. Resilient arm (134) may be suitably resilient such that when resilient arm (134) is pivoted into the flexed position, the closure force between jaws (112, 114) is sufficient such that electrodes (113, 115) may properly seal tissue grasped between jaws (112, 114). Additionally, the resilient nature of arm may limit the amount of closure force between jaws (112, 114) such that jaws (112, 114) may not compress tissue too much, resulting in inadvertent tissue damage. When the operator no longer desires to compress tissue between jaws (112, 114) to properly seal clamped tissue, the operator may reduce the amount of closure force applied to resilient arm (134) such that arm (134) returns to the relaxed state.

Housing (132) slidingly supports an RF trigger (142) of electrode activation assembly (140). RF trigger (142) is in communication with control unit (104). RF trigger (142) may be pressed or actuated to command control unit (104) to supply RF energy to electrodes (113, 115) of end effector (110). RF trigger (142) may electrically couple with control unit (104) through any suitable components known to a person having ordinary skill in the art in view of the teachings herein.

As will be described in greater detail below, firing assembly (150) is configured to actuate knife (120) within jaws (112, 114) from a proximal position to a distal position in order to sever tissue captured between jaws (112, 114). Previous firing assemblies for electrosurgical forceps may have had a trigger that was a lever arm configured to rotate relative to a handle assembly to actuate a knife. The lever arm may have extended away from the handle assembly in order to provide a mechanical advantage for actuating knife within jaws (112, 114). However, when lever arm extends away from handle assembly, it may become difficult rotate lever arm when instrument is flipped such that thumb ring becomes finger rings and vice versa. In such instances when instrument is flipped, the lever arm may no longer associate with the index/middle finger for actuating the lever arm.

Therefore, it may be desirable to have a compact firing assembly with a trigger close to the center of housing such that it is easy to actuate firing assembly with the same finger(s), even when instrument is flipped. Firing assembly (150) of the current example includes a knife trigger (152) slidably coupled with housing (132) via a slot (135). Trigger (152) is close to the center of housing (132) such that trigger (152) may be easily accessed regardless if instrument (100) is flipped around. Trigger (152) may actuate relative to housing (132) in order to actuate a knife (120) of end effector (110). In particular, proximal translation of trigger (152) results in distal translation of knife (120), while distal translation of trigger (152) results in proximal translation of knife (120). Trigger (152) may be biased toward the distal position such that knife (120) is biased toward the proximal position.

Trigger (152) may be coupled with knife (120) through any suitably firing mechanism assembly as would be apparent to one having ordinary skill in the art in view of the teachings herein. It should be understood that trigger (152) may be selectively actuated at any suitable time the operator desires. For instance, the operator may grasp tissue by pivoting jaws (112, 114) to the closed position, wait a desired amount of time, and fire trigger (152) to actuate knife (120) and sever tissue. Alternative, the operator may grasp tissue by pivoting jaws (112, 114), release tissue if jaws (112, 114) are not satisfactorily grasping tissue, re-grasp tissue, and then fire trigger (152) to actuate knife (120) and sever tissue.

Figure 3A:
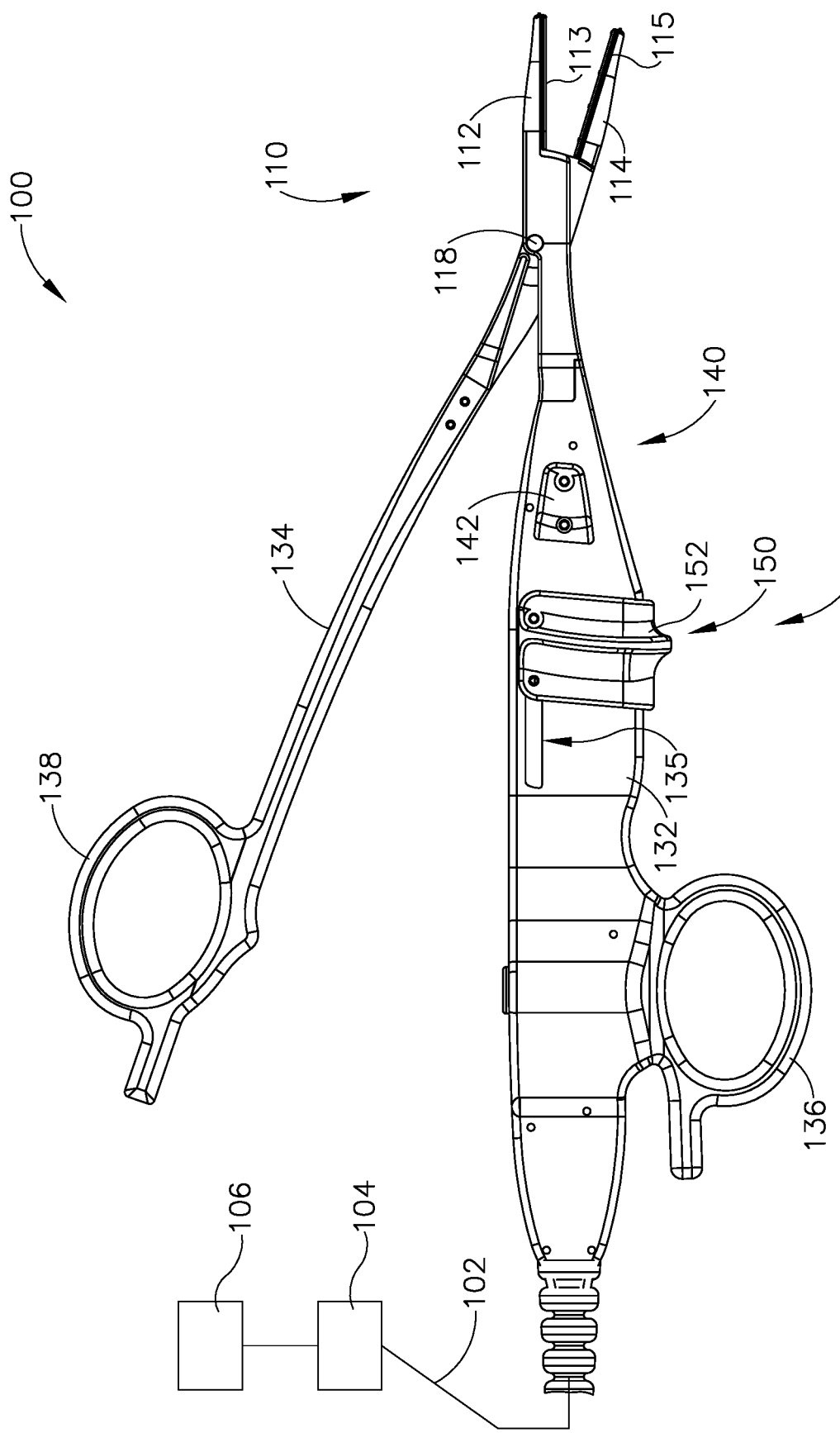
FIG. 3A depicts a side elevational view of the electrosurgical forceps instrument of FIG. 1, where the end effector is in the opened position, where the resilient arm is in the relaxed position, and where the translating knife of FIG. 2 is in the proximal position.
Figure 3B:
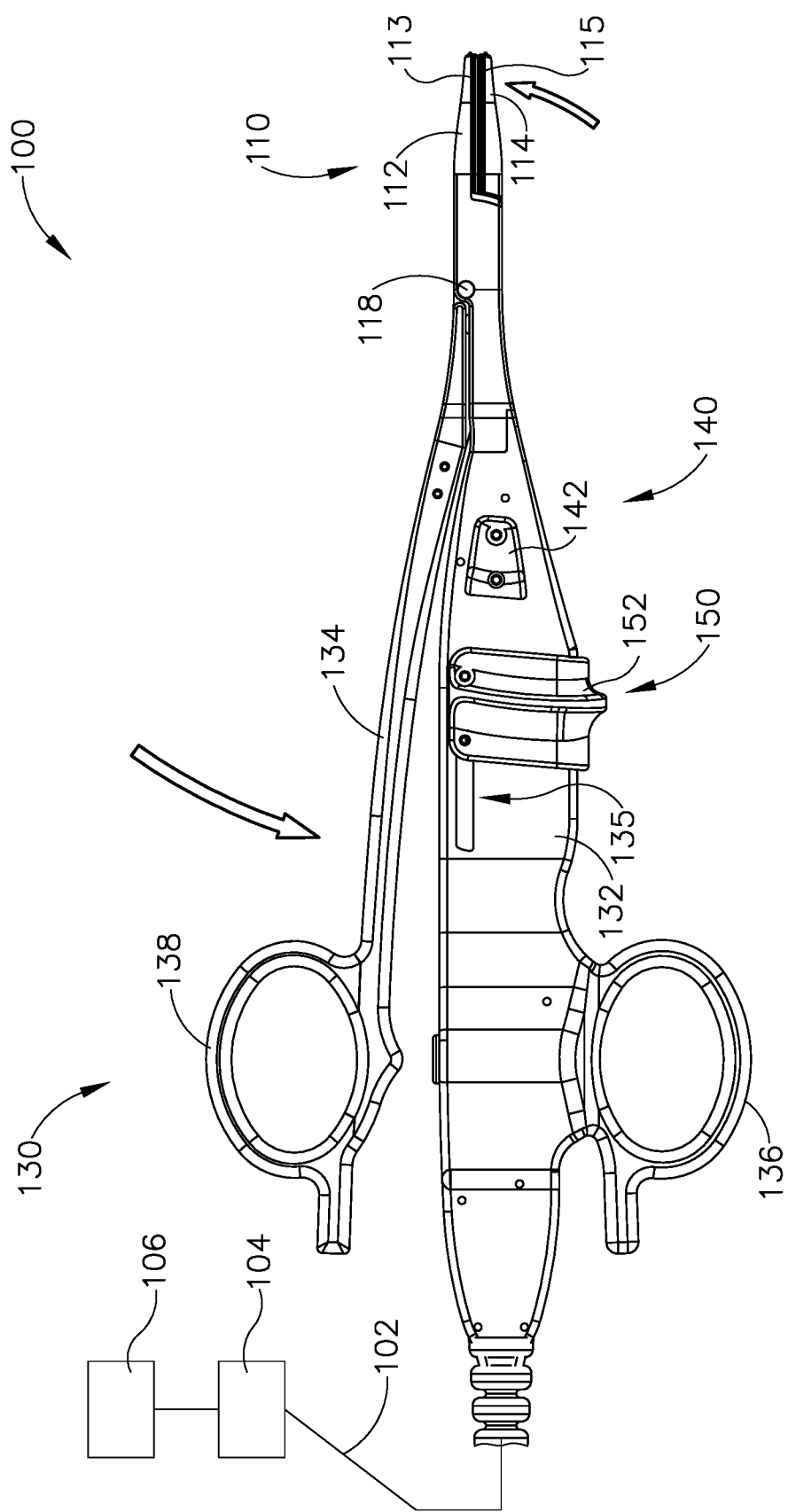
FIG. 3B depicts a side elevational view of the electrosurgical forceps instrument of FIG. 1, where the end effector is in the closed position, where the resilient arm is in the relaxed position, and where the translating knife of FIG. 2 is in the proximal position.

FIGS. 3A-4B show an exemplary operation of instrument (100). FIG. 3A shows jaws (112, 114) of end effector (110) in the opened position. Therefore, resilient arm (134) is pivoted away from housing (132). As shown in FIG. 3B, when the operator desires to initially grasp and manipulate tissue, the operator may pivot resilient arm (134) toward housing (132) such that jaws (112, 114) are pivoted toward the closed position while resilient arm (134) remains in the relaxed position. With jaws (112, 114) pivoted toward the closed position, the operator may manipulate tissue grasped by jaws (112, 114). It should be understood that the closure forces imparted on tissue by jaws (112, 114) at this point may not be sufficient enough for suitable sealing of tissue via RF energy provided by electrodes (113, 115).

Figure 3C:
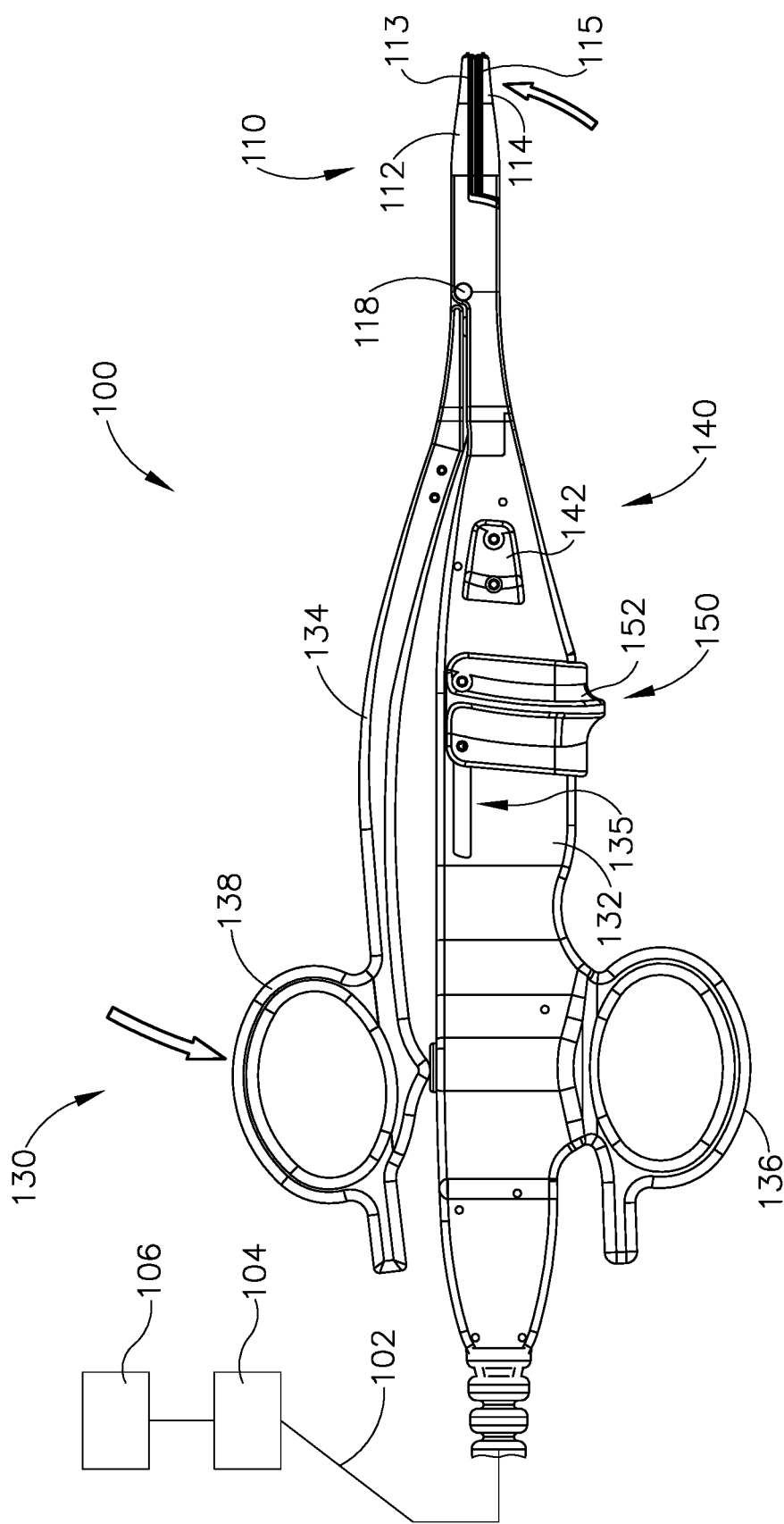
FIG. 3C depicts a side elevational view of the electrosurgical forceps instrument of FIG. 1, where the end effector is in the closed position, where the resilient arm is in a flexed position, and where the translating knife of FIG. 2 is in the proximal position.
Figure 3D:
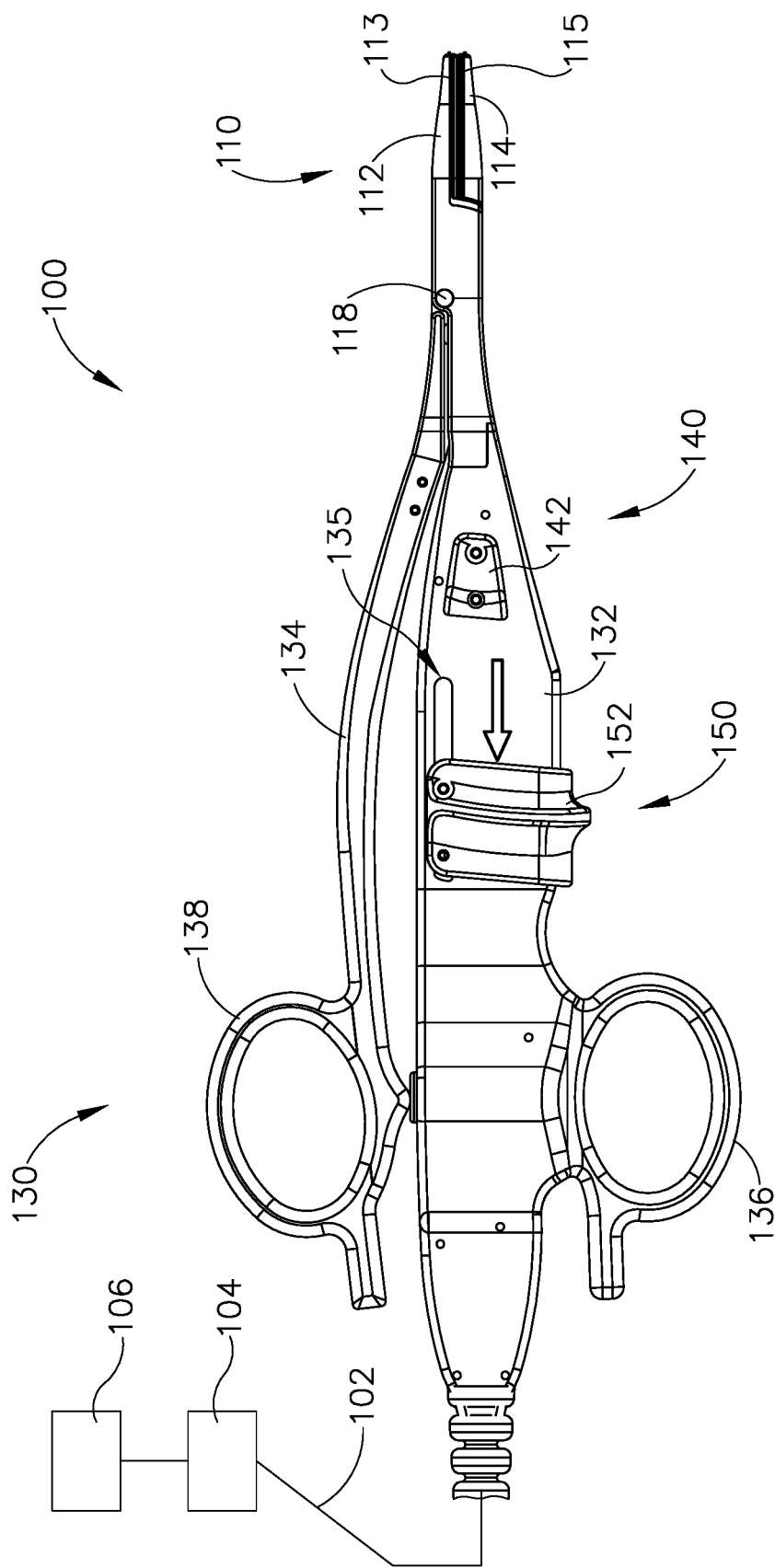
FIG. 3D depicts a side elevational view of the electrosurgical forceps instrument of FIG. 1, where the end effector is in the closed position, where the resilient arm is in the flexed position, and where the translating knife of FIG. 2 is in a distal position.

Next, as shown in FIG. 3C, if the operator desires to apply RF energy to grasped tissue, the operator may further pivot resilient arm (134) toward housing (132) such that resilient arm bends to the flexed position. As this point, the closure forces imparted on tissue by jaws (112, 114) is sufficient for proper sealing. The operator may then actuate RF trigger (142) such that electrodes (113, 115) provide RF energy to grasped tissue. Next, as shown between FIGS. 3C-3D and 4A-4B, the operator may desire to sever tissue captured between jaws (112, 114). Therefore, the operator may actuate trigger (152) proximally as shown between FIGS. 3C-3D such that knife (120) actuates distally as shown between FIGS. 4A-4B. Cutting edge (122) may sever tissue captures between jaws (112, 114) as knife (120) actuates distally through elongate slot (116).

While in the current example, the operator applies RF energy to grasped tissue and then subsequently severs the tissue, the operator may alternatively sever grasped tissue first, then apply RF energy to the tissue as would be apparent to one of ordinary skill in the art in accordance with the teachings herein. Alternatively, the operator may only seal grasped tissue by applying RF energy, without severing the tissue, as would be apparent to one of ordinary skill in the art in accordance with the teachings herein. Alternately, the operator may only sever grasped tissue, without sealing the tissue, as would be apparent to one of ordinary skill in the art in accordance with the teachings herein. Alternatively, the operator may just grasp tissue, without severing or sealing the tissue, as would be apparent to one of ordinary skill in the art in accordance with the teachings herein.

II. Alternative Exemplary Electrosurgical Forceps

As mentioned above, it may be desirable to have a compact firing assembly with a trigger close to the center of the housing such that it is easy to actuate firing assembly regardless of whether the instrument is flipped. Therefore, it may be desirable to have various firing assemblies that are configured to convert proximal translation of a sliding trigger into distal translation of a knife in order to sever tissue.

As also mentioned above, resilient arm (134) may flex toward housing (132) when jaws (112, 114) are in the closed position to provide greater closure forces between jaws (112, 114). The closure forces provided by flexing resilient arm (134) may help activated electrodes (113, 115) properly seal tissue grasped between jaws (112, 114). During exemplary use, if the operator fails to generate enough closure force while jaws (112, 114) are in the closed position, electrodes (113, 115) may fail to properly seal tissue grasped between jaws (112, 114). Therefore, it may be desirable to provide a lockout assembly that indicates when jaws (112, 114) provide a suitable closure force for sealing grasped tissue or prevents electrodes (113, 115) from activating unless jaws (112, 114) provide a suitable closure force for sealing grasped tissue.

In some instances, the operator may accidentally actuate knife trigger (152) proximally while jaws (112, 114) are open, inadvertently exposing distal cutting edge (122) of knife (120) within slot (116). Therefore, it may be desirable to provide a lockout mechanism that prevents actuation of knife until jaws (112, 114) are sufficiently closed. Alternatively, the operator may properly actuate knife (120) distally while jaws (112, 114) are suitably grasping tissue, and then prematurely open jaws (112, 114) such that distal cutting edge (122) is inadvertently exposed within slot (116). Inadvertent exposure of distal cutting edge (122) within slot (116) while jaws (112, 114) are open may cause accidental tissue damage. Therefore, it may be desirable to prevent exposure of distal cutting edge (122) after distally firing knife (120) through jaws (112, 114) by having an automatic knife return mechanism configured to automatically drive knife (120) to a pre-fired position after knife (120) reaches a predetermined distal position.

While various examples of firing assemblies, lockout assemblies, and knife return mechanisms are described below, it should be understood various combinations or modifications may be made to such firing assemblies, lockout assemblies, and knife return mechanism as would be apparent to one having ordinary skill in the art in view of the teachings herein.

Figure 5:
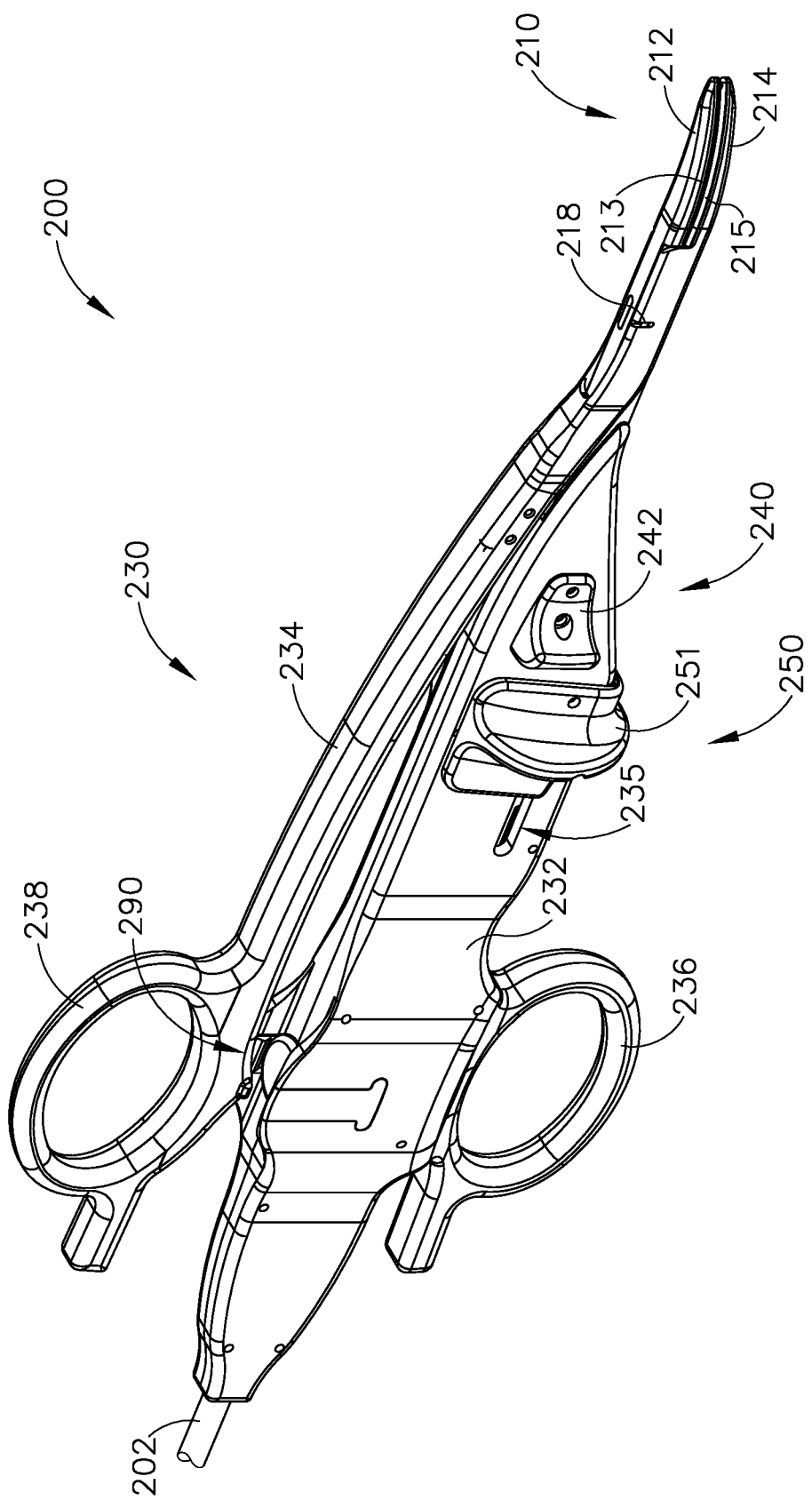
FIG. 5 depicts a perspective view of another exemplary electrosurgical forceps instrument, where an end effector is in a closed position, and where a resilient arm is in a relaxed position.

FIG. 5 shows an alternative exemplary electrosurgical forceps instrument (200) that may be used in replacement of instrument (100) described above. Therefore, as will be described in greater detail below, instrument (200) may be used to grasp, seal, and sever tissue.

Instrument (200) includes an end effector (210), a handle assembly (230), an electrode activation assembly (240), a firing assembly (250), and a lockout assembly (290). End effector (210) is substantially similar to end effector (110) described above, with differences elaborated below. End effector (210) includes a first jaw (212) having a first electrode (213), a second jaw (214) having a second electrode (215), and a knife (220) configured to translate through the first jaw (212) and the second jaw (214).

Figure 6:
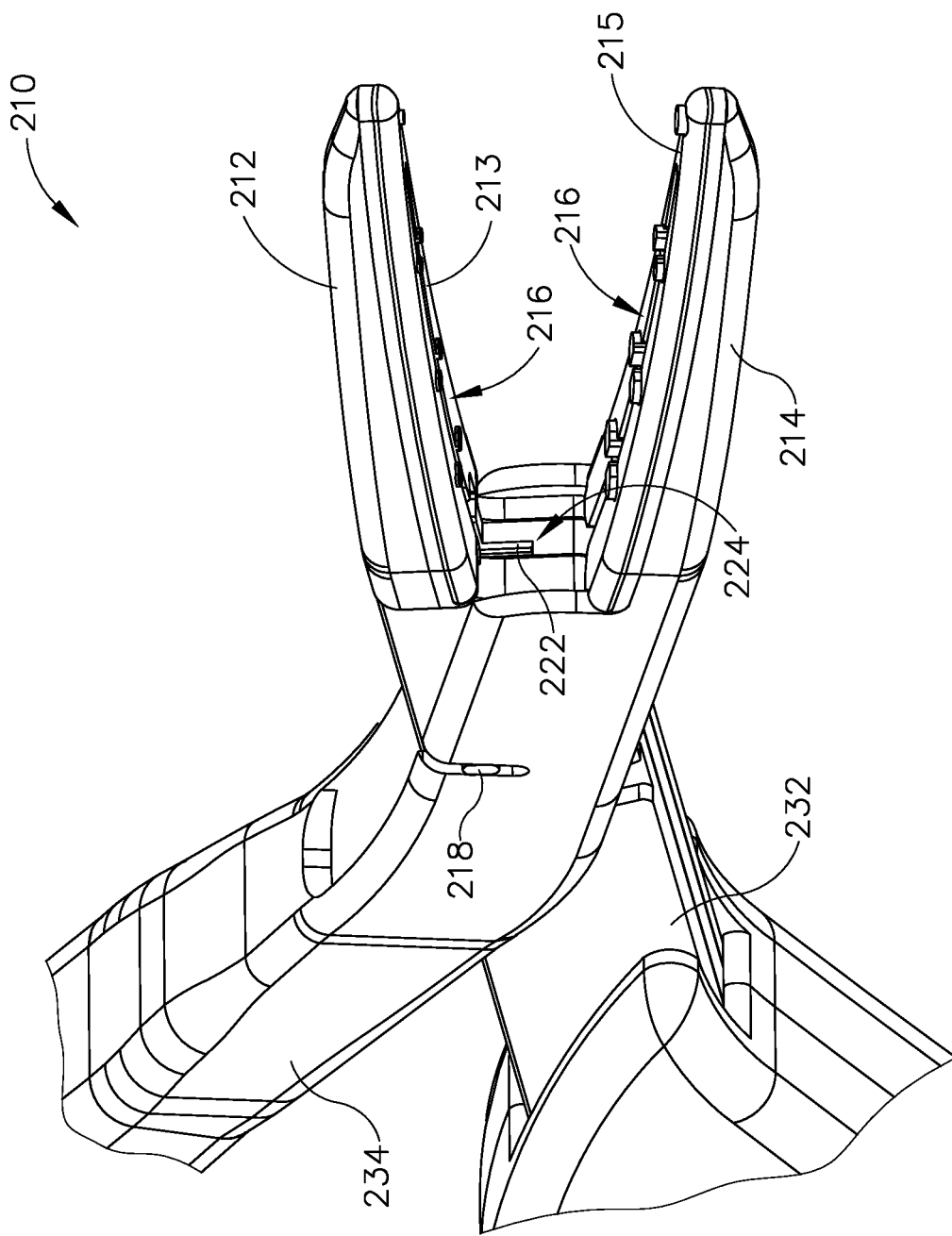
FIG. 6 depicts a perspective view of the end effector of FIG. 5 in an opened position, where a translating knife is in a proximal position.
Figure 7:
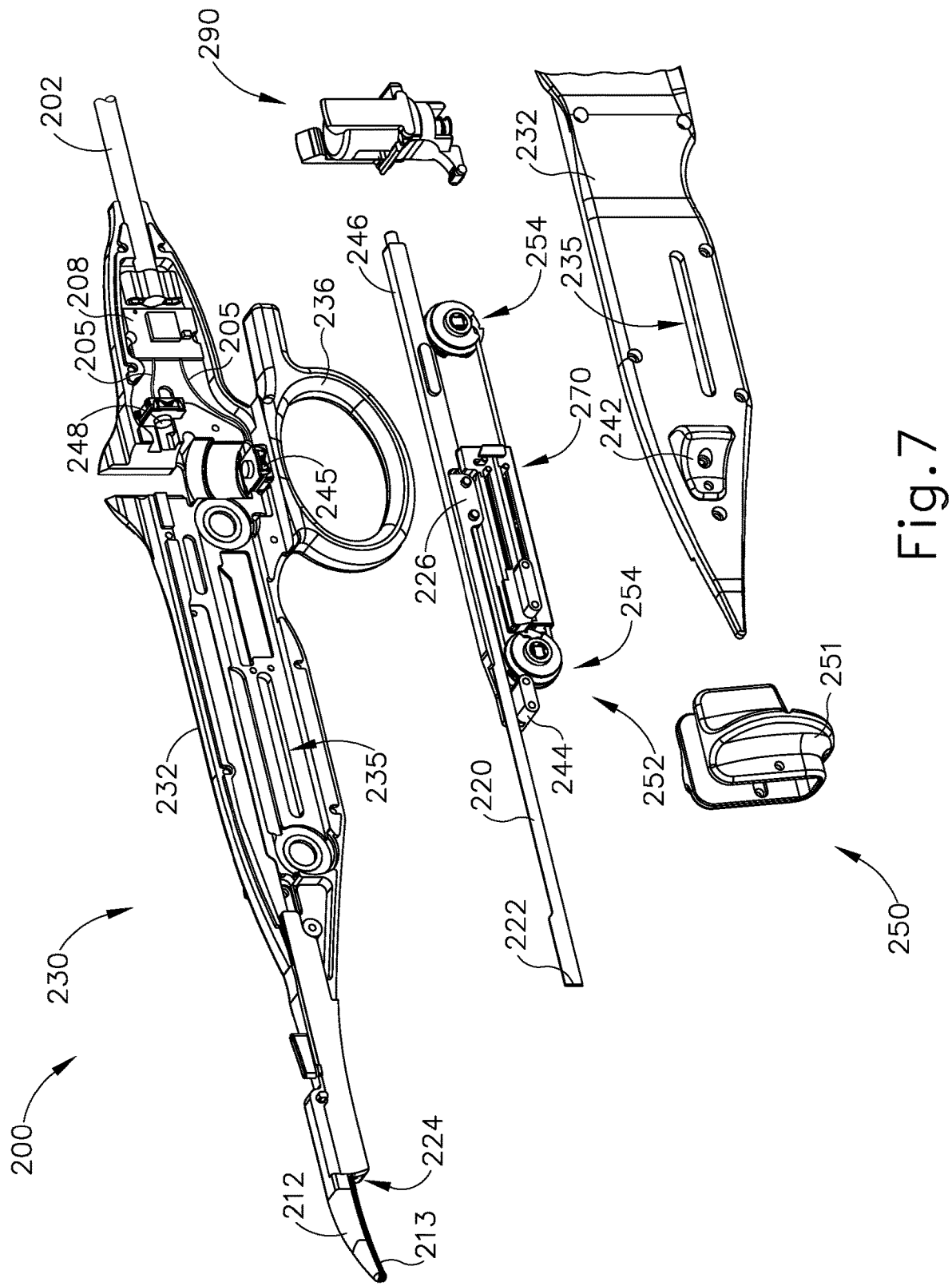
FIG. 7 depicts an exploded perspective view of a handle assembly of the electrosurgical forceps instrument of FIG. 5.
Figure 9:
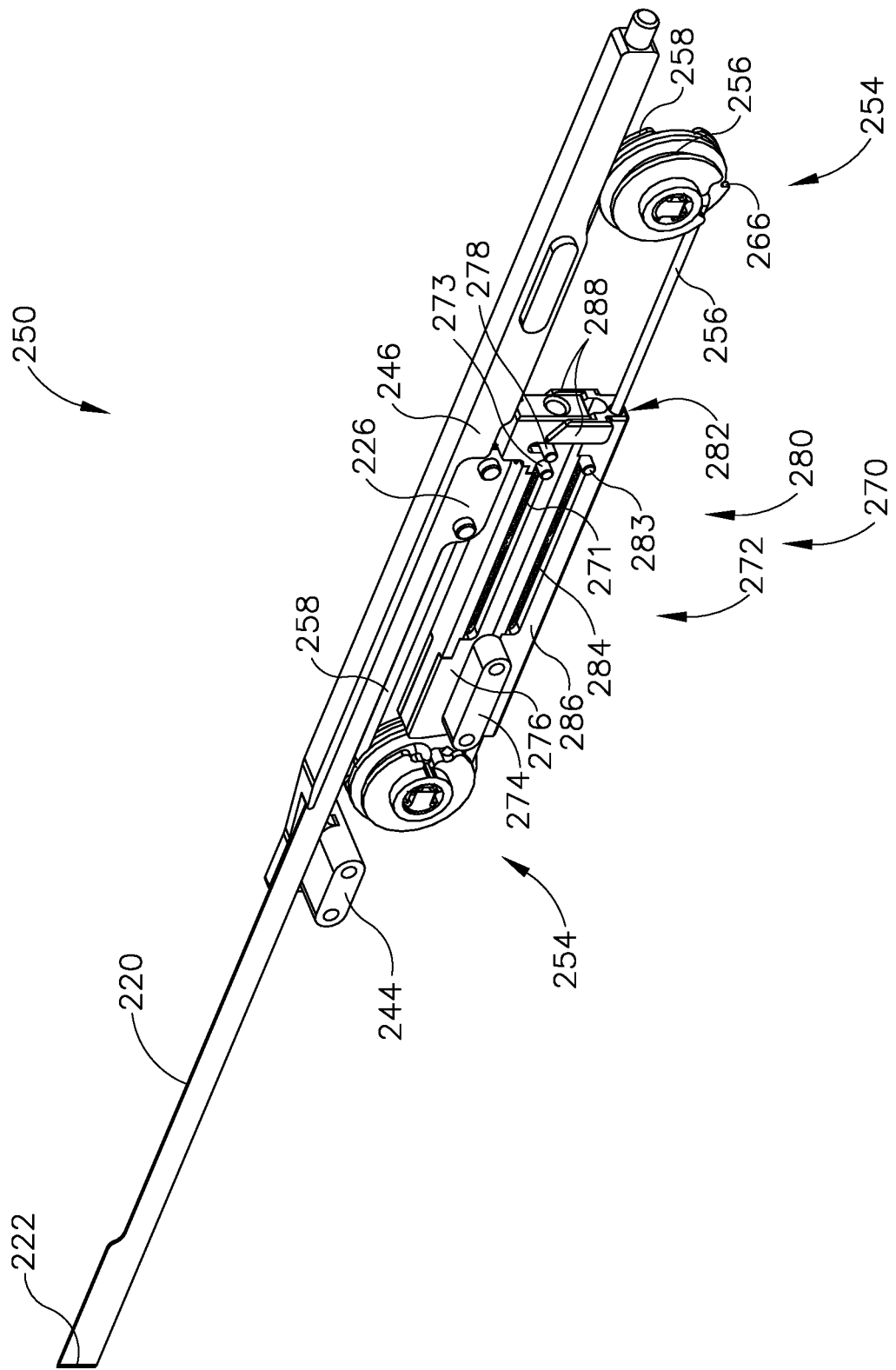
FIG. 9 depicts a perspective view of a firing assembly of the electrosurgical forceps instrument of FIG. 5.
Figure 10:
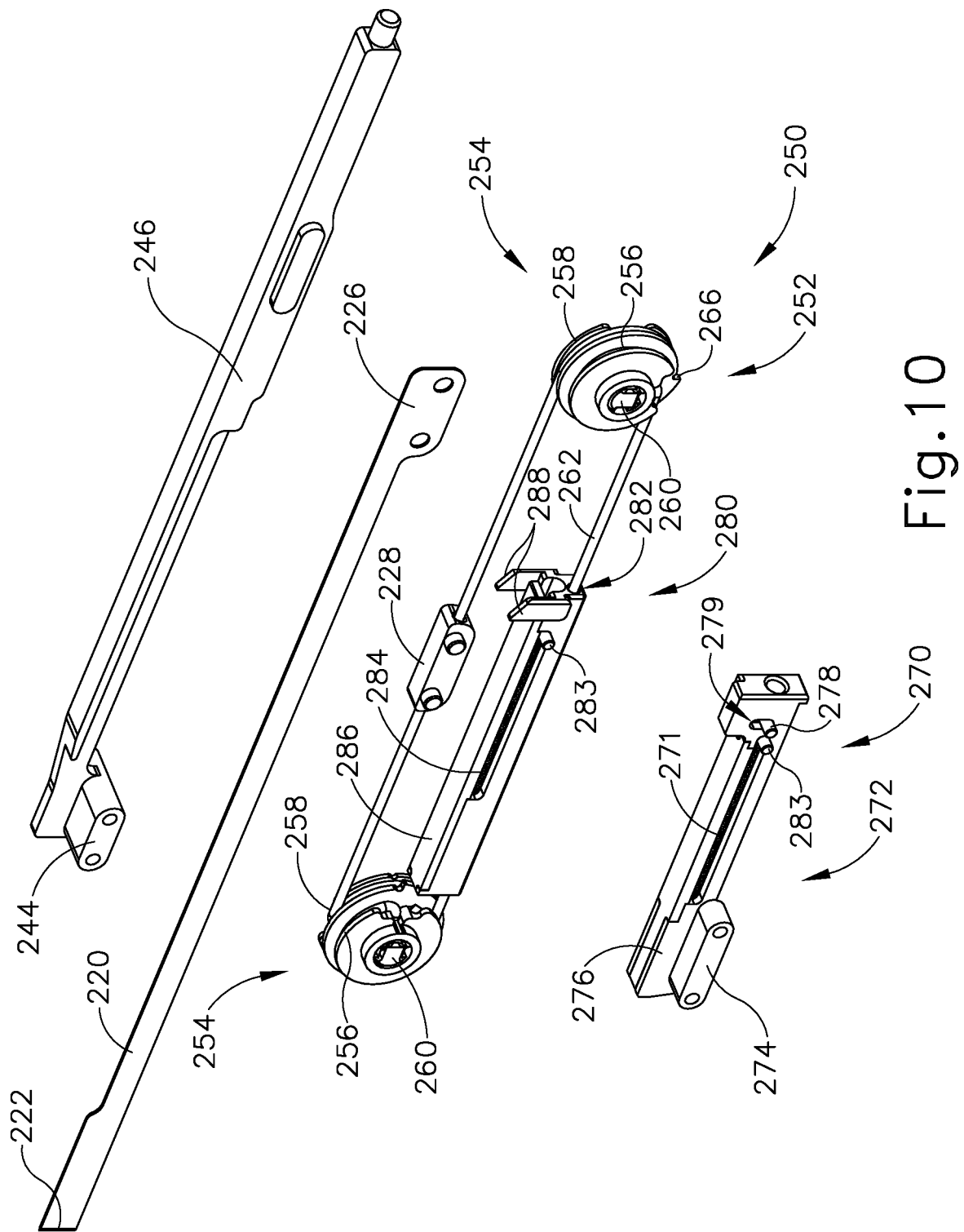
FIG. 10 depicts an exploded perspective view of the firing assembly of FIG. 9.

First jaw (212) and second jaw (214) are pivotably coupled with each other via pivot pin (218). First jaw (212) and second jaw (214) may pivot between an open position (FIG. 6) and a closed position (FIG. 5) in order to grasp tissue. First and second electrodes (213, 215) are positioned on respective jaws (212, 214) such that electrodes (213, 215) face each other when jaws (212, 214) are pivoted into the closed position. Additionally, each electrode (213, 215) is U-shaped in the present example, with the bend of the U-shape located near the distal end of each respective jaw (212, 214), such that each electrode (213, 215) includes two longitudinally extending, laterally spaced-apart legs extending along the length of each respective jaw (212, 214). Laterally spaced-apart legs of each electrode (213, 215) and corresponding portions of jaws (212, 214) define an elongate slot (216). Elongate slot (216) is dimensioned to slidably receive knife (220) such that knife may translate from a proximal position to a distal position, similar to knife (120) described above. As best shown in FIGS. 7, 9, and 10, knife (220) includes a distal cutting edge (222) configured to sever tissue captured between jaws (212, 214) in the closed position.

A cable (202) extends proximally from handle assembly (230). Similar to cable (102) of instrument (100), cable (202) is configured to couple with control unit (104), which is further coupled with a power source (106). Therefore, control unit (104) is operable to provide RF power to electrodes (213, 215) of jaws (212, 214), to thereby seal tissue suitably captured between jaws (212, 214).

Handle assembly (230) includes a housing (232) and a resilient arm (234). Housing (232) and resilient arm (234) are substantially similar to housing (122) and resilient arm (134) described above, with differences elaborated below. Housing (232) and resilient arm (234) are pivotably coupled with each other via pivot pin (218). Housing (232) extends distally into first jaw (212), while resilient arm (234) extends distally into second jaw (214). Housing defines a knife pathway (224) that slidably houses a portion of knife (220). Housing (232) includes a finger ring (236) while resilient arm (234) terminates proximally into a thumb ring (238). Therefore, the operator may grasp instrument (200) in a scissor grip fashion and pivot resilient arm (234) relative to housing (232) via rings (236, 238) in order to open and close jaws (212, 214).

Resilient arm (234) is substantially similar to resilient arm (134) described above. Therefore, resilient arm (234) is sufficiently resilient such that arm (234) may flex from a relaxed position to a flexed position in response to pivoting arm (234) further toward housing (232) when jaws (212, 214) are already in the closed position. Resilient arm (234) is biased toward the relaxed position. Further pivoting of resilient arm (234) into the flexed position may result in greater closure forces between jaws (212, 214) as compared to pivoting jaws (212, 214) into the closed position while arm (234) is in the relaxed position. Resilient arm (234) may be suitably resilient such that when resilient arm (234) is pivoted into the flexed position, the closure force between jaws (212, 214) is sufficient such that electrodes (213, 215) may properly seal tissue grasped between jaws (212, 214). Additionally, the resilient nature of arm (234) may limit the amount of closure force between jaws (212, 214) such that jaws (212, 214) may not compress tissue too much, resulting in inadvertent tissue damage. When the operator no longer desires to compress tissue between jaws (212, 214) to properly seal or sever clamped tissue, the operator may reduce the amount of closure force applied to resilient arm (234) such that arm (234) returns to the relaxed state.

Housing (232) contains electrode activation assembly (240), firing assembly (250), and lockout assembly (290). Firing assembly (250) of the current example includes a knife trigger (251) slidably coupled with housing (232) via a slot (235). As will be described in greater detail below, electrode activation assembly (240) is configured to selectively activate electrodes (213, 215); firing assembly (250) is configured to actuate knife (220) between the proximal position and the distal position (Similar to knife (120) as shown in FIGS. 4A-4B) in response to proximal translation of knife trigger (251) within slot (235); and lockout assembly (290) is configured to prevent actuation of knife (220) until specific conditions are satisfied. In some examples, lockout assembly (290) may be configured to prevent activation of electrodes (213, 215) until specific conditions are satisfied, or indicate when jaws (212, 214) are sufficiently closed for suitably sealing tissue. As will also be described in greater detail below, a portion of firing assembly (250) and handle assembly (230) form an automatic knife return mechanism configured to automatically drive knife (220) to the proximal, pre-fired, position after knife (220) reaches a predetermined distal position.

Electrode activation assembly (240) includes an RF trigger (242) slidably supported on each lateral side of housing (232), a sliding body (246) slidably contained within housing (232), a coupling block (244) fixed relative to sliding body (246), an activation button (248), and a lockout button (245). Coupling block (244) is configured to couple with each RF trigger (242) when instrument (200) is assembled. A proximal end of sliding body (246) is directly adjacent to activation button (248) such that proximal translation of sliding body (246) triggers activation button (248). Therefore, the operator may press RF trigger (242) proximally in order to compress activation button (248). RF trigger (242), coupling block (244), and/or sliding body (246) may be biased toward a position such that activation button (248) is not activated.

Activation button (248) and lockout button (245) are each contained within housing (232). Lockout button (245) and activation button (248) are each in communication with a circuit board (208) via electrical coupling wires (205); while circuit board (208) is also in communication with at least one electrode (213, 215) via electrical coupling wires (205). In the present example, circuit board (208) is contained within housing (232). Circuit board (208) is in communication with cable (202) such that circuit board (208) and control unit (104) are in electrical communication with each other. Therefore, circuit board (208) is configured to transfer RF energy from control unit (104) to electrodes (213, 215). As will be described in greater detail below, lockout assembly (290) is configured to depress lockout button (245) when jaws (212, 214) are sufficiently closed to provide sufficient closure force to properly seal tissue captured between electrodes (213, 215) using RF energy.

In one example, activation button (248) and lockout button (245) are configured to instruct circuit board (208) to transfer RF energy from control unit (104) to electrodes (213, 215) when buttons (245, 248) are depressed. If only one, or neither, button (245, 248) is depressed, circuit board (208) will not transfer RF energy to electrodes (213, 215), thereby leaving electrodes (213, 215) deactivated. Therefore, for example, if the operator pressed RF trigger (242) without having lockout button (245) depressed, electrodes (213, 215) will remain deactivated. Alternatively, lockout button (245) may act as a switch for activation button (248) such that activation of lockout button (245) completes a circuit between at least one electrode (213, 215) and activation button (248).

In another example, lockout button (245) may only generate a signal to circuit board (208), which may then send the signal to control unit (104), that jaws (212, 214) are sufficiently closed to provide sufficient closure force to properly seal tissue captured between electrodes (213, 215) using RF energy. Control unit (104) may then signal to the operator (i.e. visually, audibly, or tactilely) that jaws (212, 214) are sufficiently closed. In such examples, activation button (248) may independently instruct circuit board (208) to transfer RF energy from control unit (104) to electrodes (213, 215) when activation button (248) is depressed.

In another example, depression of either activation button (248) or lockout button (245) may be configured to activate electrodes (213, 215), but activation of buttons (245, 248) may send a different signal to control unit (104), such that control unit produces a different signal (i.e. visually, audibly, or tactilely) indicating to a user which button (245, 248) has been depressed.

In yet another example, activation button (248) may be omitted entirely such that pressing lockout button (245) leads to activation of electrodes (213, 215).

While in the current example, circuit board (208) acts as an intermediary between control unit (104), electrodes (213, 215), and buttons (245, 248), this is merely optional, as buttons (245, 248) and electrodes (213, 215) may be in communication with cable (202) and control unit (104) without the use of circuit board (208).

Figure 8:
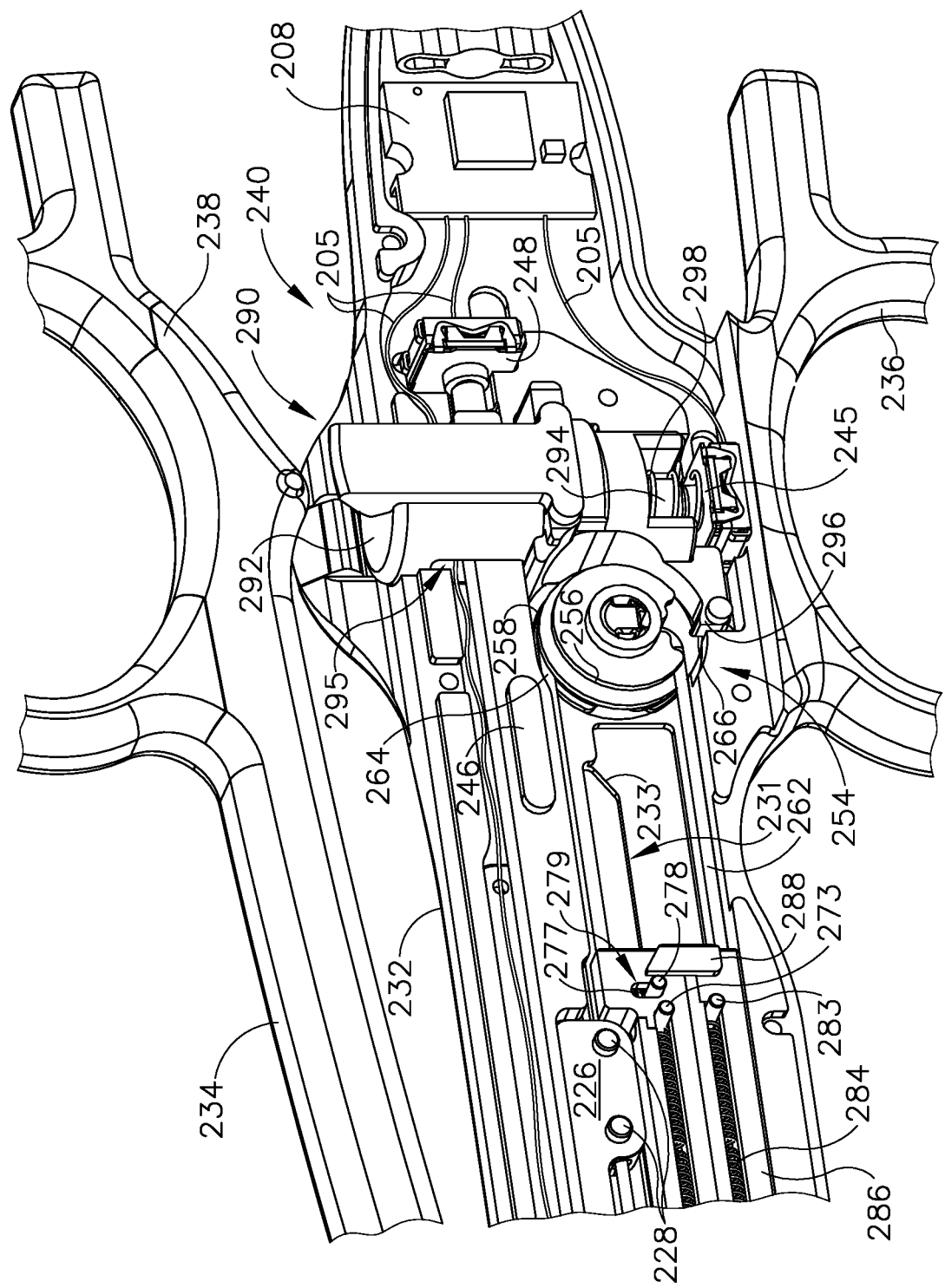
FIG. 8 depicts a perspective view of a portion of the forceps instrument of FIG. 5, with a portion of the handle assembly of FIG. 7 omitted for clarity, where a lockout assembly is in a locked configuration, where the resilient arm is in the relaxed position.

As mentioned above, lockout assembly (290) is configured to either indicate when jaws (212, 214) are sufficiently closed or prevent activation of electrodes (213, 215) until jaws (212, 214) are sufficiently closed; while lockout assembly (290) is also configured to prevent actuation of knife (220) until specific conditions are satisfied. As best seen in FIG. 8, lockout assembly (290) includes a translating body (292) defining a through hole (295), and a bias spring (298). Translating body (292) includes a button (294) extending downwardly from the rest of body (292), and a lockout ledge (296) extending distally from the rest of body (292). Translating body (292) is slidably disposed within housing (232). Translating body (292) is configured to actuate between a locked position (as shown in FIGS. 8 and 15A) to an unlocked position (as shown in FIGS. 15B-15F); while bias spring (298) abuts against an interior portion of housing (132) and translating body (292) to bias translating body (292) toward the locked position.

Figure 15A:
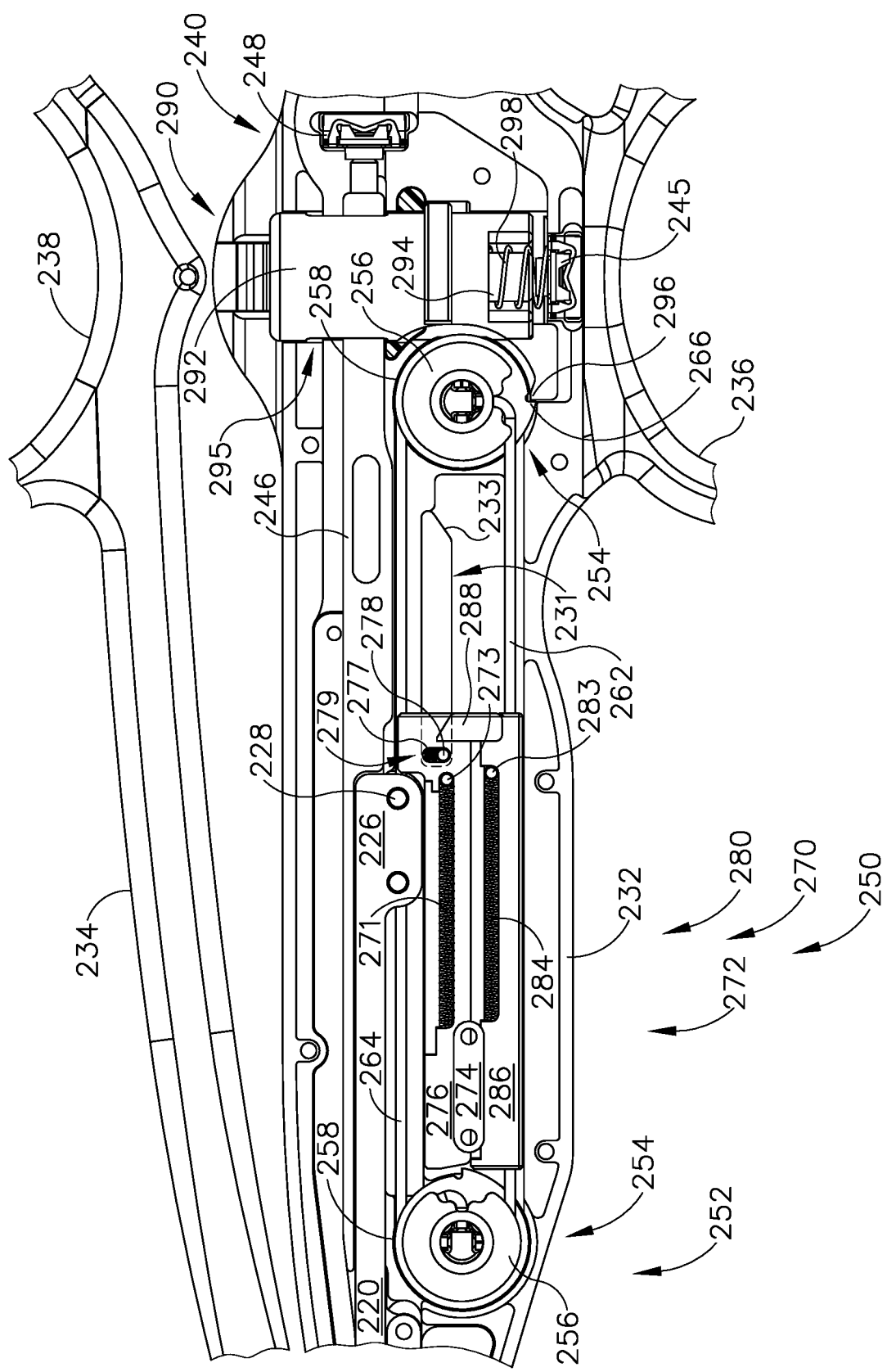
FIG. 15A depicts a side elevational view of a portion of the instrument of FIG. 5, with a portion of the handle assembly of FIG. 7 omitted for clarity, where the end effector is in the closed position, where the resilient arm is in a relaxed position, where the lockout assembly of FIG. 8 is in a locked configuration, and where the firing assembly of FIG. 9 is in a first pre-fired position.

As best seen in FIGS. 8 and 15A, a portion of translating body (292) extends away from housing (232) toward thumb ring (238) while in the locked position. Thumb ring (238) of resilient arm (234) is dimensioned to abut against the portion of translating body (292) extending away from housing (232) when resilient arm (234) is in the flexed position, thereby driving lockout assembly (290) into the unlocked position. Thumb ring (238) does not abut against the portion of translating body (292) extending away from housing (232) when resilient arm (234) is in the relaxed position, such that spring (298) biases translating body (292) into the locked position.

As described above, the closure forces provided by jaws (212, 214) when resilient arm (234) is in the flexed position are suitable for electrodes (213, 215) to seal tissue via RF energy. Therefore, lockout assembly (290) is configured to move into the unlocked position when jaws (212, 214) provide a suitable closure force for electrodes (213, 215) to seal tissue via RF energy. Additionally, lockout assembly (290) is configured to move into the locked position when jaws (212, 214) do not provide a suitable closure force for electrodes (213, 215) to seal tissue via RF energy.

While in the unlocked position, button (294) depresses lockout button (245) of electrode activation assembly (240), thereby rendering lockout button (245) activated. Therefore, in one example, if the operator presses RF trigger (242) while lockout assembly (290) is in the unlocked position, circuit board (208) would activate electrodes (213, 215) dues to both buttons (248, 245) being depressed. In other words, the operator is permitted to activate RF energy to electrodes (213, 215) when the closure forces provided by jaws (212, 214) are suitably conducive for sealing tissue via RF energy. In another example, lockout button (245) generates a signal send to control unit (104). An in yet another example, depressing lockout button (245) instructs circuit board (208) to activate electrode (213, 215).

Also, while in the unlocked position, lockout ledge (296) is spaced away from an angular lockout projection (266) of firing assembly (250) such that firing assembly (250) may actuate knife (220) in accordance with the description herein. Therefore, when lockout assembly (290) is in the unlocked position, the operator may both activate electrodes (213, 215) with RF energy, and actuate knife (220) distally to sever tissue grasped between jaws (212, 214). Lockout assembly (290) may indicate to the operator when lockout assembly (290) is in the unlocked configuration. For example, depressing button (245) may activate a suitable indicator as would be apparent to one having ordinary skill in the art in view of the teachings herein. For example, an LED may turn on, an instrument may emit noise, or a tactile response may be felt.

While in the locked position, button (294) is spaced away from lockout button (245) of electrode activation assembly (240), thereby rendering lockout button (245) un-activated. Therefore, in the example where both lockout button (245) and activation button (248) must be depressed to activate electrodes (213, 215), if the operator presses RF trigger (242) while lockout assembly (290) is in the locked position, either accidentally or in an attempt to provide RF energy to electrodes (213, 215), circuit board (208) would not activate electrodes (213, 215) due to both buttons (248, 245) not being depressed. In other words, the operator is prevented from activating RF energy to electrodes (213, 215) when the closure forces provided by jaws (212, 214) are not suitably conducive for sealing tissue via RF energy (i.e. resilient arm (234) is in the relaxed position).

Also, while in the locked position, lockout ledge (296) is directly adjacent to angular lockout projection (266) of firing assembly (250), thereby preventing actuation of firing assembly (250) while body (292) is in the locked position. As will be described in greater detail below, angular lockout projection (266) is fixed to a pulley drive assembly (252) configured to rotate in order to distally translate knife (220). Since lockout ledge (296) prevents rotation of angular lockout projection (266) while lockout assembly (290) is in the locked position, lockout ledge (296) also prevents distal translation of knife (220) while lockout assembly (290) is in the locked position. In other words, when lockout assembly (290) is in the locked position, the operator may be prevented from activating electrodes (213, 215) with RF energy, as well as prevented from distally actuating knife (220) to sever tissue.

Through hole (295) is dimensioned to allow suitable portions of electrode activation assembly (240) to actuate within through hole (295). In the current example, one through hole (295) allows sliding body (246) of electrode activation assembly (240) to actuate within through hole (295) to access activation button (248).

As mentioned above, firing assembly (250) is configured to convert proximal translation of trigger (251) into distal translation of knife (220). As also mentioned above, a portion of firing assembly (250) and handle assembly (230) form an automatic knife return mechanism configured to automatically drive knife (220) to a pre-fired position after knife (220) reaches a predetermined distal position. Firing assembly (250) includes an input drive assembly (270), a pulley drive assembly (252), and an output drive assembly, such as output coupling block (228) coupled with a proximal body (226) of knife (220). As will be described in greater detail below, trigger (251) is configured to actuate input drive assembly (270) proximally such that pulley drive assembly (252) actuates output coupling block (228) and knife (220) distally. It should be understood that sliding body (246) of electrode activation assembly (240) may slide independently relative to firing assembly (250). Therefore, the operator may activate electrodes (213, 215) independently of firing assembly (250) and knife (220), in accordance with the description herein.

Input drive assembly (270) includes a first sliding member (272) and a second sliding member (280). Both sliding members (272, 280) are slidably contained within housing (232). As will be described in greater detail below, first sliding member (272) is configured to proximally drive second sliding member (280), while second sliding member (280) is configured to actuate pulley drive assembly (252).

As best seen in FIGS. 8-10, first sliding member (272) includes a coupling block (274), a sliding body (276), a transverse driving pin (278), a grounding pin (273), a first biasing member (271) disposed within the confines of sliding body (276) against grounding pin (273), and a second biasing member (277) housed within a slot (279) defined by sliding body (276). Sliding body (276) is slidably contained within housing (232) such that sliding body (276) may translate within housing (232) but may not rotate relative to housing (232). Coupling block (274) is fixed relative to sliding body (276). Coupling block (274) is configured to couple with trigger (251) when instrument (200) is assembled such that actuation of trigger (251) relative to housing (232) drives actuation of coupling block (274) and sliding body (276) relative to housing (232).

Figure 15B:
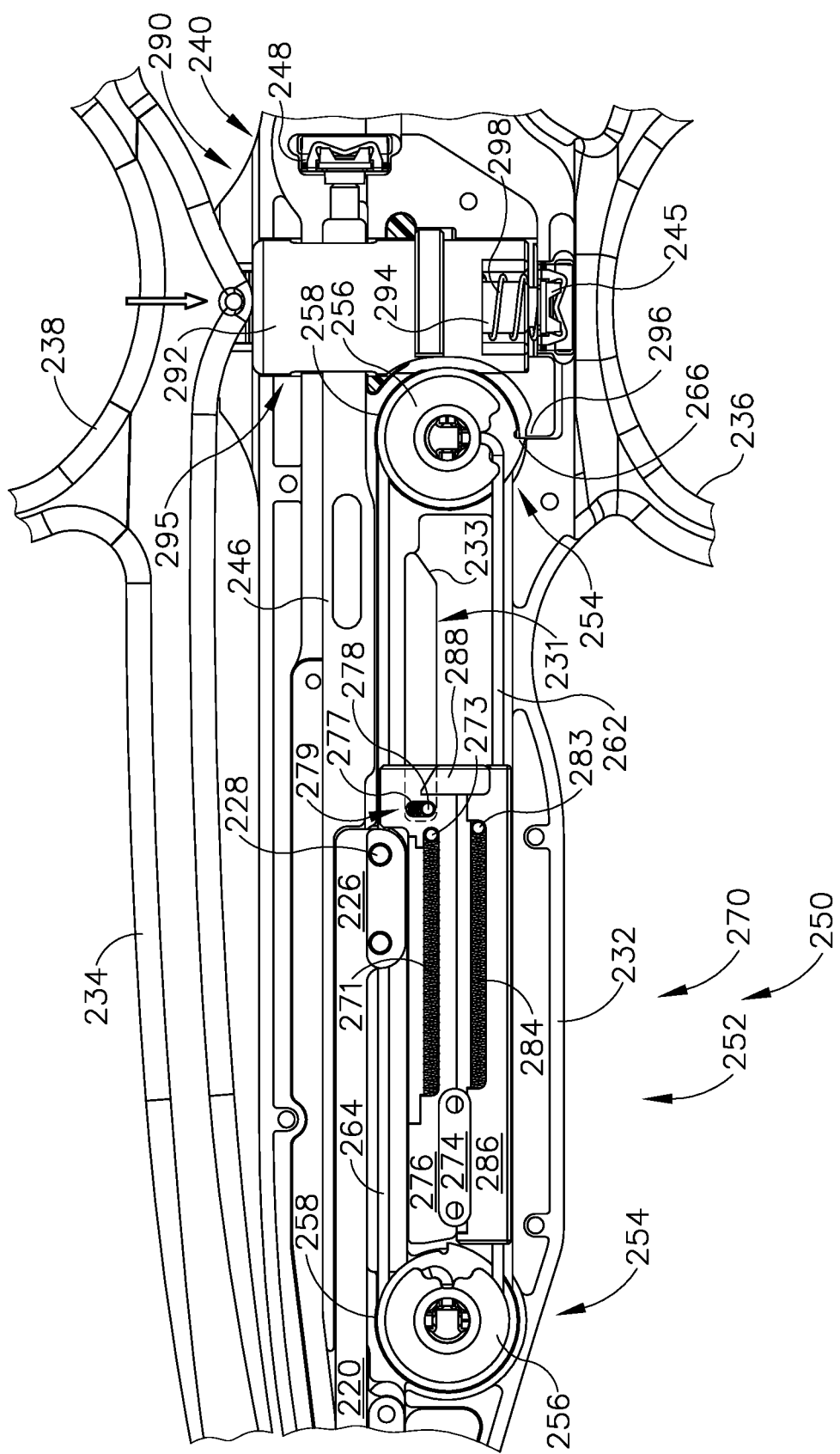
FIG. 15B depicts a side elevational view of a portion of the instrument of FIG. 5, with a portion of the handle assembly of FIG. 7 omitted for clarity, where the end effector is in the closed position, where the resilient arm is in a flexed position, where the lockout assembly of FIG. 8 is in an unlocked configuration, and where the firing assembly of FIG. 9 is in the first pre-fired position.

As will be described in greater detail below, transverse driving pin (278) is dimensioned to drive portions of second sliding member (280) proximally in response to proximal translation of first sliding member (272). As will also be described in greater detail below, transverse driving pin (278) is slidable within slot (279) such that transverse driving pin (278) may selectively disassociate with second sliding member (280) such that second sliding member (280) automatically returns to a distal position associated with knife (220) being in a pre-fired position. Grounding pin (273) is fixed to housing (232) when instrument (200) is assembled such that as sliding body (276) translates, grounding pin (273) remains spatially fixed relative to housing (232). Biasing member (271) abuts against grounding pin (273) and sliding body (276) in order to bias sliding body (276) to a distal, pre-fired position (as shown in FIGS. 15A-15B and 15F). Therefore, if the operator actuates trigger (251) and sliding body (276) proximally, biasing member (271) compresses such that when the operator releases trigger (251), biasing member (271) actuates trigger (251) back to the distal, pre-fired, position. In the current example, biasing member (271) includes a spring, but any other suitable biasing member (271) may be used as would be apparent to one having ordinary skill in the art in view of the teachings herein.

Second sliding member (280) includes a sliding body (286), a grounding pin (283), a biasing member (284) disposed within the confines of sliding body (286), and a pair of laterally spaced projections (288). Additionally, sliding body (286) defines a pathway (282). Sliding body (286) is fixed to an input cable (262) that extends through pathway (282). Laterally spaced projections (288) are fixed to sliding body (286). Sliding body (286) is slidably contained within housing (232) such that sliding body (286) may translate within housing (232) but may not rotate relative to housing (232). As will be described in greater detail below, projections (288) are dimensioned to abut against transverse driving pin (278) such that first sliding member (272) may proximally drive second sliding member (280). As will also be described in greater detail below, sliding body (286) is configured to actuate relative to housing (232) to thereby drive rotation of pulley drive assembly (252) such that translation of sliding body (286) in one direction leads to translation of knife (220) in the opposite direction. Grounding pin (283) is fixed to housing (232) when instrument (200) is assembled such that as sliding body (286) translates, grounding pin (283) remains spatially fixed relative to housing (232). Biasing member (284) abuts against grounding pin (283) and sliding body (286) in order to bias sliding body (286) to a distal, pre-fired position (as shown in FIGS. 15A-15B, and 15F).

As mentioned above, sliding body (276) defines a slot (279) that slidably houses transverse driving pin (278). Second biasing member (277) biases transverse driving pin (278) to a downward position within slot (279). Transverse driving pin (278) may actuate within slot (279) to overcome the biasing force of second biasing member (277). Transverse driving pin (278) is dimensioned to abut against projections (288) of first sliding member (272) when second biasing member (277) biases transverse driving pin (278) in the downward position. Therefore, if the operator actuates trigger (251) proximally, first sliding member (272) may proximally drive second sliding member (280) via projections (288) and transverse driving pin (278). Additionally, as best shown in FIGS. 15A-15F, transverse driving pin (278) is housed within a slotted pathway (231) defined by the interior of housing (232). Therefore, as transverse driving pin (278) drives projections (288), a portion of pin (278) is within slotted pathway (231). As will be described in greater detail below, once first and second sliding members (272, 280) proximally translate a predetermined distance, transverse driving pin (278) may actuate within slot (289), due to contact with a cam surface (233) of slotted pathway (231), such that transverse driving pin (278) no longer engages projections (288). Therefore, with projections (288) no longer engaged with driving pin (278), first biasing member (284) may distally drive sliding body (286) back to the distal, pre-fired position, which in turn may rotate pulley drive assembly (252) to actuate knife (220) back into the pre-fired position.

Output coupling block (228) is fixed to an output cable (264). Additionally, output coupling block (228) is fixed to proximal body (226) of knife (220) via an interference fit between complementary holes and protrusions. When instrument (200) is assembled, output coupling block (228) and translating knife (220) may actuate relative to housing (232) together. While in the current example, proximal body (226) of knife (220) is fixed to output coupling block (228) via protrusions and holes in an interference fit, any other suitably coupling means may be utilized as would be apparent to one having ordinary skill in the art in view of the teachings herein.

Output coupling block (228) is slidably contained within housing (232) such that output drive body (228) may translate relative to housing (232) but not rotate relative to housing (232). As will be described in greater detail below, pulley drive assembly (252) is configured to drive output coupling block (228) in the opposite direction of sliding body (286) in response to sliding body (286) driving pulley drive assembly (252).

Figure 11:
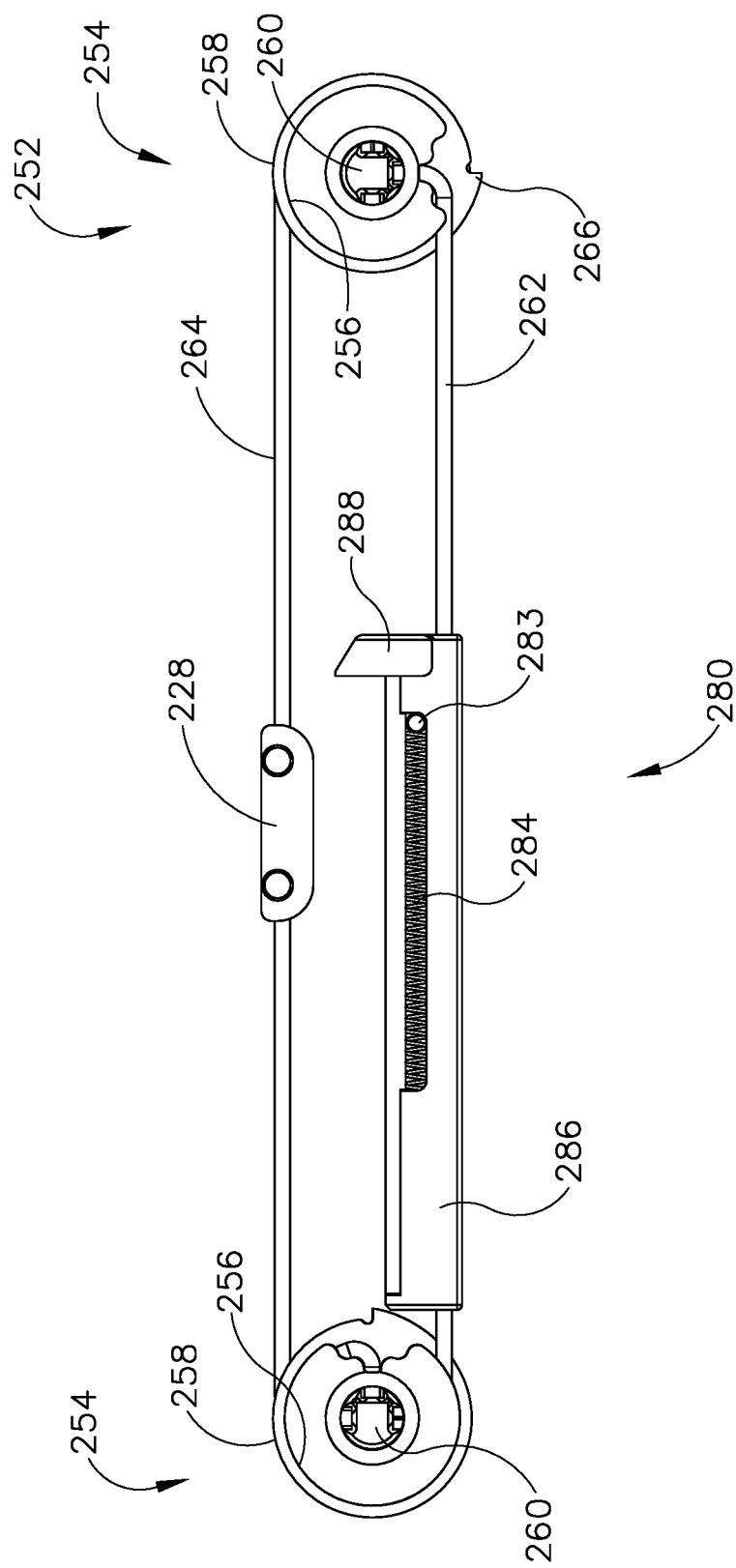
FIG. 11 depicts a side elevational view of a rotary drive assembly of the firing assembly of FIG. 9.
Figure 12:
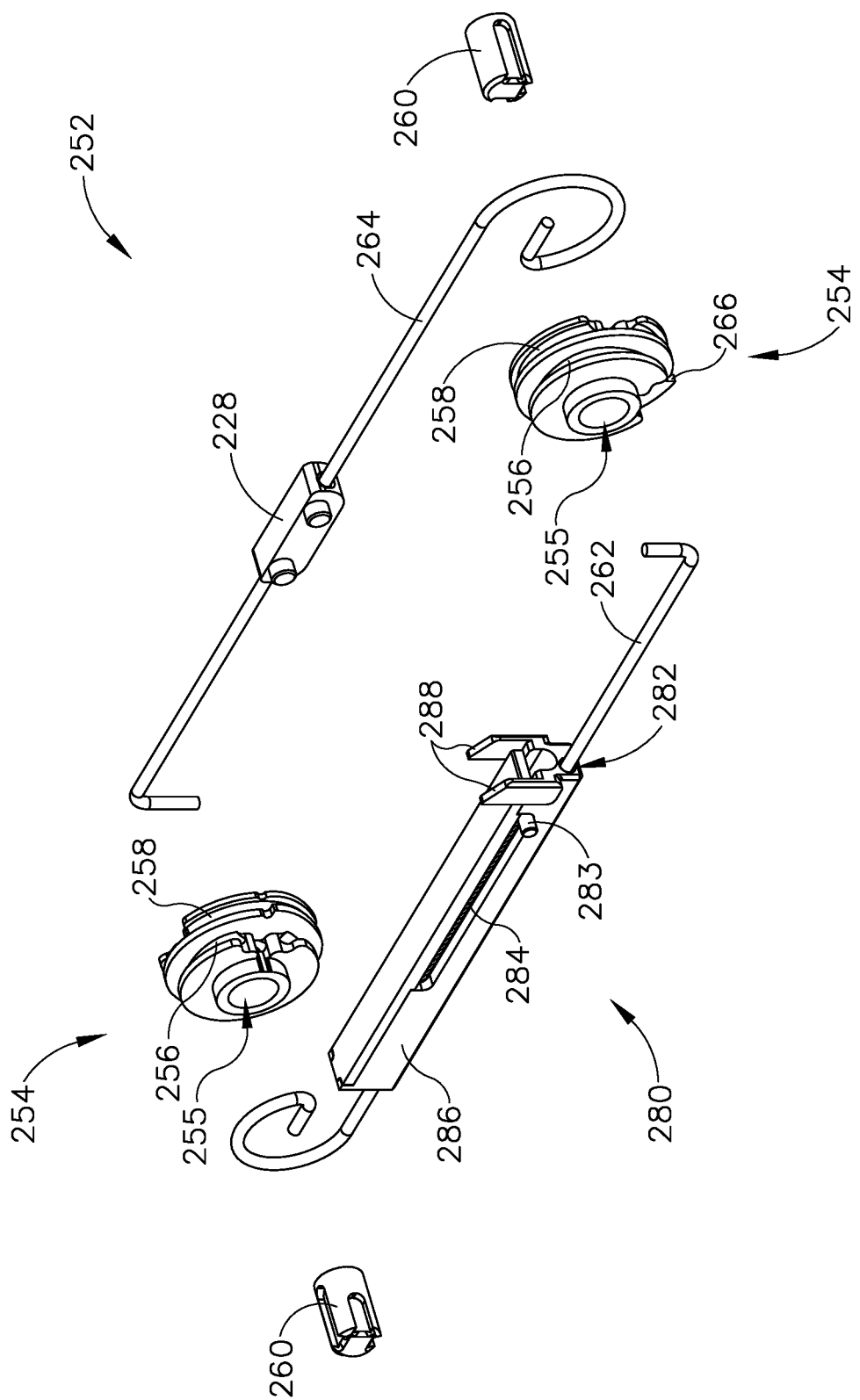
FIG. 12 depicts an exploded perspective view of the rotary drive assembly of FIG. 11.
Figure 14:
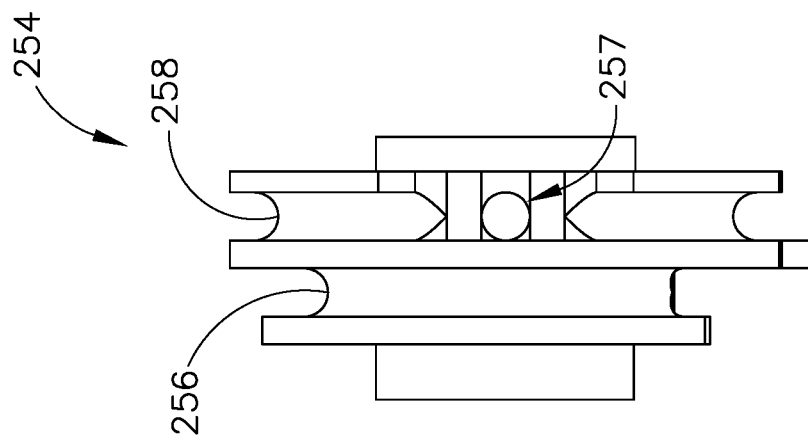
FIG. 14 depicts a top plan view of the compound pulley wheel of FIG. 13.
Figure 13:
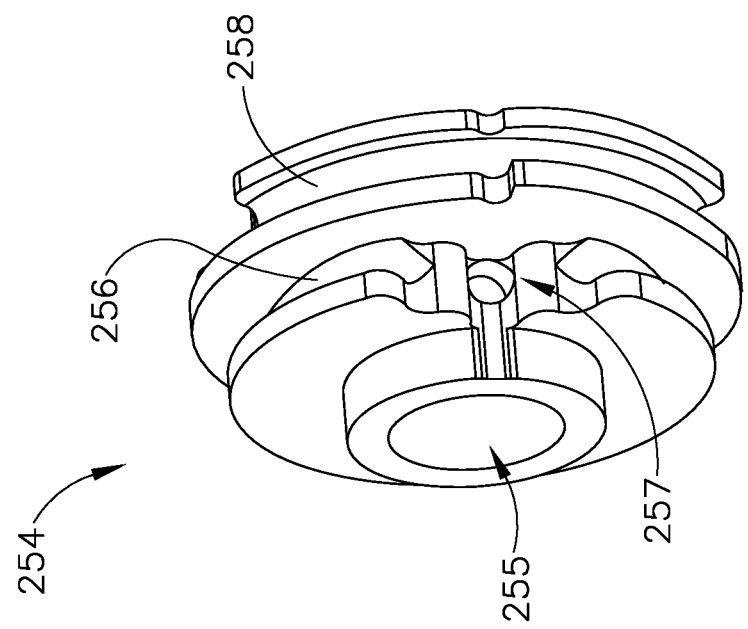
FIG. 13 depicts a perspective view of a compound pulley wheel of the rotary drive assembly of FIG. 11.

As best shown in FIGS. 11-12, pulley drive assembly (252) includes two compound pulley wheels (254), input cable (262), output cable (264), and a core (260) for each respective wheel (254). Compound pulley wheels (254) are rotatably disposed within housing (232) such that wheels (254) may rotate within housing (232) but may not translate relative to housing (232). The proximal compound pulley wheel (254) includes angular lockout projection (266). As best shown in FIG. 13, each compound pulley wheel (254) includes an input track portion (256) and an output track portion (258). Each track portion (256, 258) defines a respective radial through hole (257) extending into transverse through hole (255). Input track portion (256) and output track portion (258) of an individual wheel (254) are unitarily connected to each other such that both track portions (256, 258) of an individual wheel (254) rotate relative to housing (232) together. Input track portion (256) has a smaller diameter than output track portion (258). Therefore, if compound pulley wheels (254) are angularly displaced, output track portion (258) will travel further than input track portion (256).

Input track portion (256) is configured to receive input cable (262); while output track portion (258) is configured to receive output cable (264). In particular, cables (262, 264) extend between respective track portions (256, 258) of both wheels (254) such that when compound pulley wheels (254)

rotate in one angular direction, one pulley wheel (254) unwinds cable (262, 264) while the other pulley wheel (254) winds up cables (262, 264) in respective track portions (256, 258). Additionally, input cable (262) extends between input track portions (256) on one side of compound pulley wheels (254), while output cable (264) extends between output track portions (258) on the opposite side of compound pulley wheels (254). Therefore, translation of input cable (262) in one linear direction drives angular rotation of compound pulley wheels (254) and simultaneously drives translation of output cable (264) in the opposite linear direction. Cables (262, 264) extend between compound pulley wheels (254) with a sufficient tension such that translation of cables (262, 264) leads to substantially responsive, consistent, and unitary angular displacement of each compound pulley wheel (254). In other words, cables (262, 264) are sufficiently taut such that translation of input cable (262) responsively and consistently drives rotation of compound pulley wheels (254) and translation of output cable (264).

Cores (260) for each respective wheel (254) couple input cable (262) with input track portion (256) and output cable (264) with output track portion (258). In particular, input cable (262) may extend through radial through hole (257) of input track portion (256) into the confines of transverse through hole (255); while output cable (264) may extend thorough radial through hole (257) of output track portion (258) into the confines of transverse through hole (255). Then core (260) may be inserted into transverse through hole (255) such that the portions of cables (262, 264) extending into radial through holes (257) are essentially fixed relative to the respective track portions (256, 258).

It should be understood that since output cable (264) is coupled with output track portions (258) and input cable (262) is coupled with input track portions (256), rotation of compound pulley wheels (254) leads to greater translation of output cable (264) as compared to input cable (262) due the track portions (256, 258) having different diameters. As mentioned above, and as shown in FIG. 11, second sliding member (280) of input drive assembly (270) is fixed to input cable (262), while output coupling block (228) is fixed to output cable (264). Therefore, if the operator actuates second sliding member (280) a first distance, in accordance with the description herein, output coupling block (228) and knife (220) will translate a second distance in the opposite direction, where the second distance is greater than the first distance. This may effectively shorten the distance knife trigger (251) must translate to drive knife (220) through jaws (212, 214).

FIGS. 15A-15F show an exemplary use of lockout assembly (290) and firing assembly (250) in accordance with the teachings herein. Similar to that shown between FIGS. 3A-3B, when the operator desires to initially grasp and manipulate tissue, the operator may pivot resilient arm (234) toward housing (232) to the position shown in FIG. 15A such that jaws (222, 214) are pivoted from the opened position toward the closed position while resilient arm (134) remains in the relaxed position. Therefore, jaws (212, 214) may not provide a sufficient closing force suitable for electrodes (213, 215) to seal tissue grasped by jaws (212, 214). With jaws (212, 214) pivoted toward the closed position, the operator may manipulate tissue grasped by jaws (212, 214). It should be understood that at this moment, knife (220) is in the pre-fired position (similar to knife (120) shown in FIG. 4A).

Additionally, as shown in FIG. 15A, thumb ring (238) does not abut against translating body (292) such that spring (298) biases translating body (292) into the locked position. At this point, if the operator actuated RF trigger (242), electrodes (213, 215) would not activate, as lockout button (245) is still deactivated. Additionally, lockout ledge (296) is directly adjacent to angular lockout projection (266), thereby preventing rotation of compound pulley wheels (254) and actuation of knife (220). Therefore, knife trigger (251) would be prevented from actuating knife (220) distally while locking assembly (290) is in the locked configuration, as sliding body (286) would not be able to rotate pulley wheels (254) to distally actuate knife (220).

Next, as seen in FIG. 15B, the operator may pivot resilient arm (234) further toward housing (232) such that resilient arm (234) bends to the flexed position. It should be understood that at this point, knife (220) is still in the pre-fired position. However, with resilient arm (234) in the flexed position, thumb ring (238) abuts against translating body (292) to overcome the biasing force provided by spring (298), such that translating body (292) is in the unlocked position. At this point, the closure forces provided by jaws (212, 214) are sufficiently suitable for electrodes (213, 215) to seal tissue grasped by jaws (212, 214). Additionally at this point, lockout button (245) is depressed such that lockout button (245) is activated in accordance with the teachings herein. While translating body (292) is in the unlocked position, lockout ledge (296) no longer interferes with rotation of angular locking body (262) of threaded body (254). Because lockout ledge (296) no longer interferes with the rotation of threaded body (254), firing assembly (250) may actuate knife (220) distally is accordance with the description herein. It should be understood that when the operator no longer presses resilient arm (234) toward housing (232) with enough force to keep arm (234) in the flexed position, the resilient nature of arm (234) will return arm (234) to the relaxed position, allowing spring (298) to bias translating body (292) back into the locked position.

Next, as shown between 15B-15C, when the operator desires to fire knife (220), the operator may pull trigger (251) proximally such that first sliding member (272) and second sliding member (280) move proximally together due to transverse driving pin (288) making contact with projections (288). Because second sliding member (280) is coupled with input cable (262), proximal actuation of second sliding member (280) drives input cable (262) proximally. As a result, the proximal compound pulley wheel (254) winds up a portion of input cable (262), while the distal compound pulley wheel (254) winds out a portion of input cable (262), thereby rotating both compound pulley wheels (254) in a first angular direction. Because output cable (264) is located on the opposite side of compound pulley wheels (252), rotation of wheels (254) in the first angular direction causes distal translation of output cable (264) such that the distal wheel (254) winds up a portion of output cable (264) and the proximal wheel (254) winds out a portion of output cable (264). Because knife (220) is coupled with output cable (264), knife (220) also actuates in the distal direction from the pre-fired position (similar to that shown in FIG. 4A) to the fired position (similar to that shown in FIG. 4B). At the moment shown in FIG. 15C, knife (220) may have actuated substantially through jaws (212, 214), severing tissue captured between jaws (212, 214), similar to the position shown of knife (120) in FIG. 4B.

Because input cable (262) is coupled with input track portions (256) and output cable (264) is coupled with output track\ portions (258), and because output track portions (258) have a greater diameter than input track portions (256), knife (220) translates a further distance distally than input drive assembly (270) actuates in the proximal direction to drive knife (220).

Because grounding pins (273, 283) are fixed relative to housing (232), movement of sliding bodies (276, 286) compresses biasing members (271, 284) between grounding pins (273, 283) and the interior of sliding bodies (276, 286), such that biasing members (271, 284) impart a distal biasing force on sliding bodies (276, 286), respectively. It should be understood that at the position shown in FIG. 15C, transverse driving pin (278) is just distal to cam surface (233) of slotted pathway (231) such that second bias member (277) is still forces transverse driving pin (278) in the downward position within slot (279). Therefore, transverse driving pin (278) is still in contact with projections (288) such that transverse driving pin (278) overcomes the distal biasing force biasing member (284) imparts on sliding body (286) to drive sliding body (286) back into the pre-fired position (as shown in FIGS. 15A-15B).

Figure 15C:
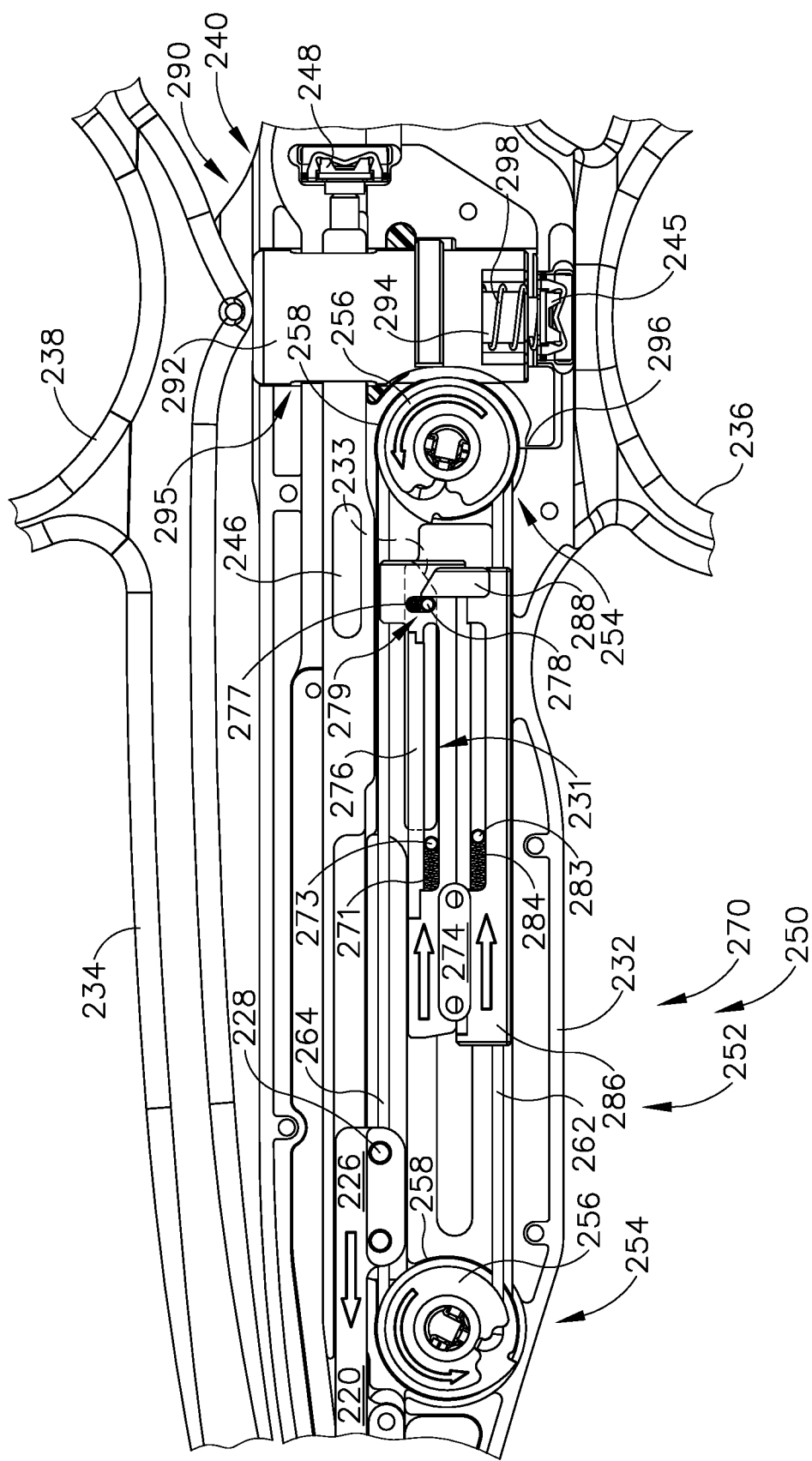
FIG. 15C depicts a side elevational view of a portion of the instrument of FIG. 5, with a portion of the handle assembly of FIG. 7 omitted for clarity, where the end effector is in the closed position, where the resilient arm is in the flexed position, where the lockout assembly of FIG. 8 is in the unlocked configuration, and where the firing assembly of FIG. 9 is in a first fired position.
Figure 15E:
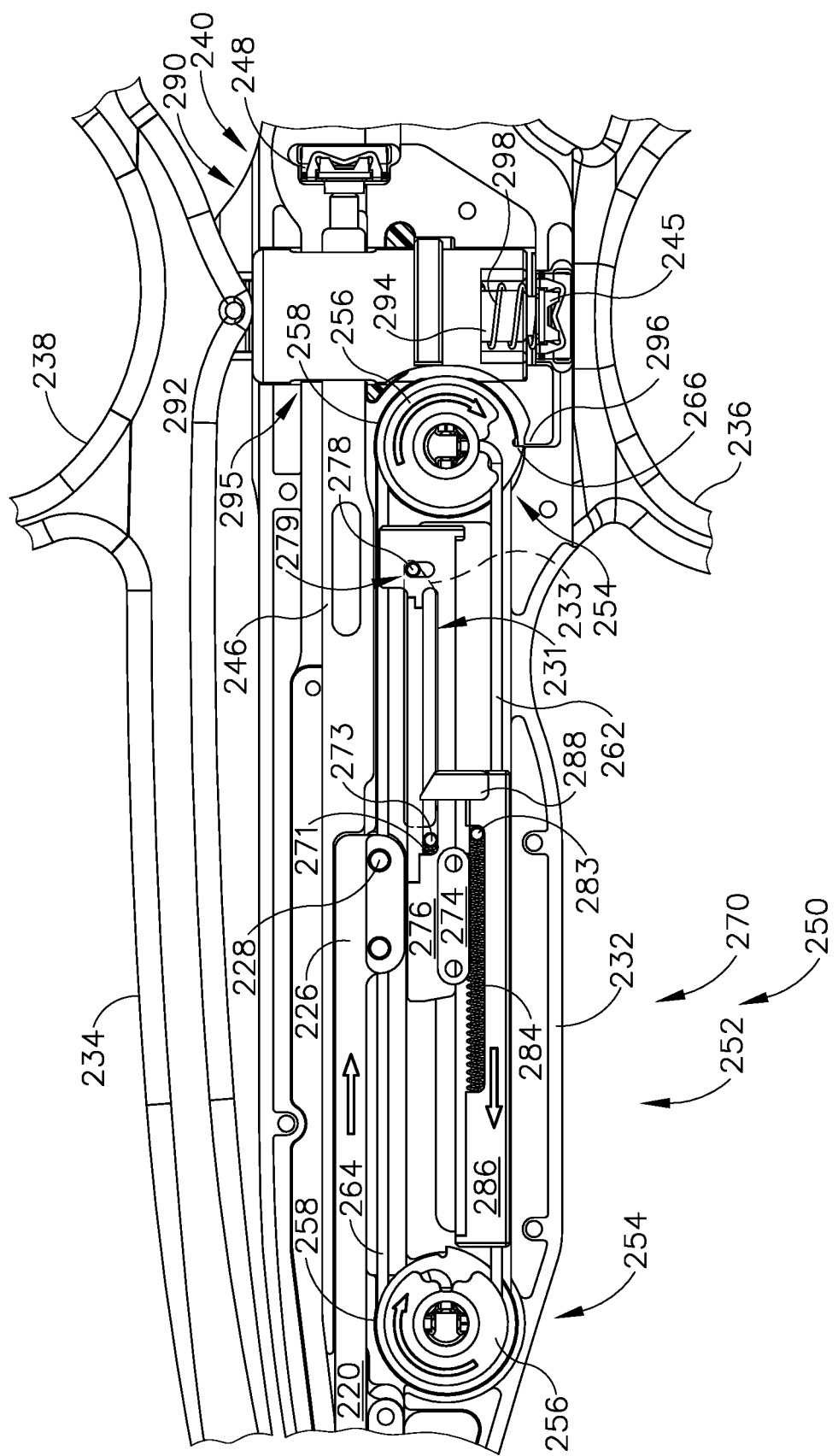
FIG. 15E depicts a side elevational view of a portion of the instrument of FIG. 5, with a portion of the handle assembly of FIG. 7 omitted for clarity, where the end effector is in the closed position, where the resilient arm is in the flexed position, where the lockout assembly of FIG. 8 is in the unlocked configuration, and where the firing assembly of FIG. 9 is in a pre-returned, post-fired position.
Figure 15F:
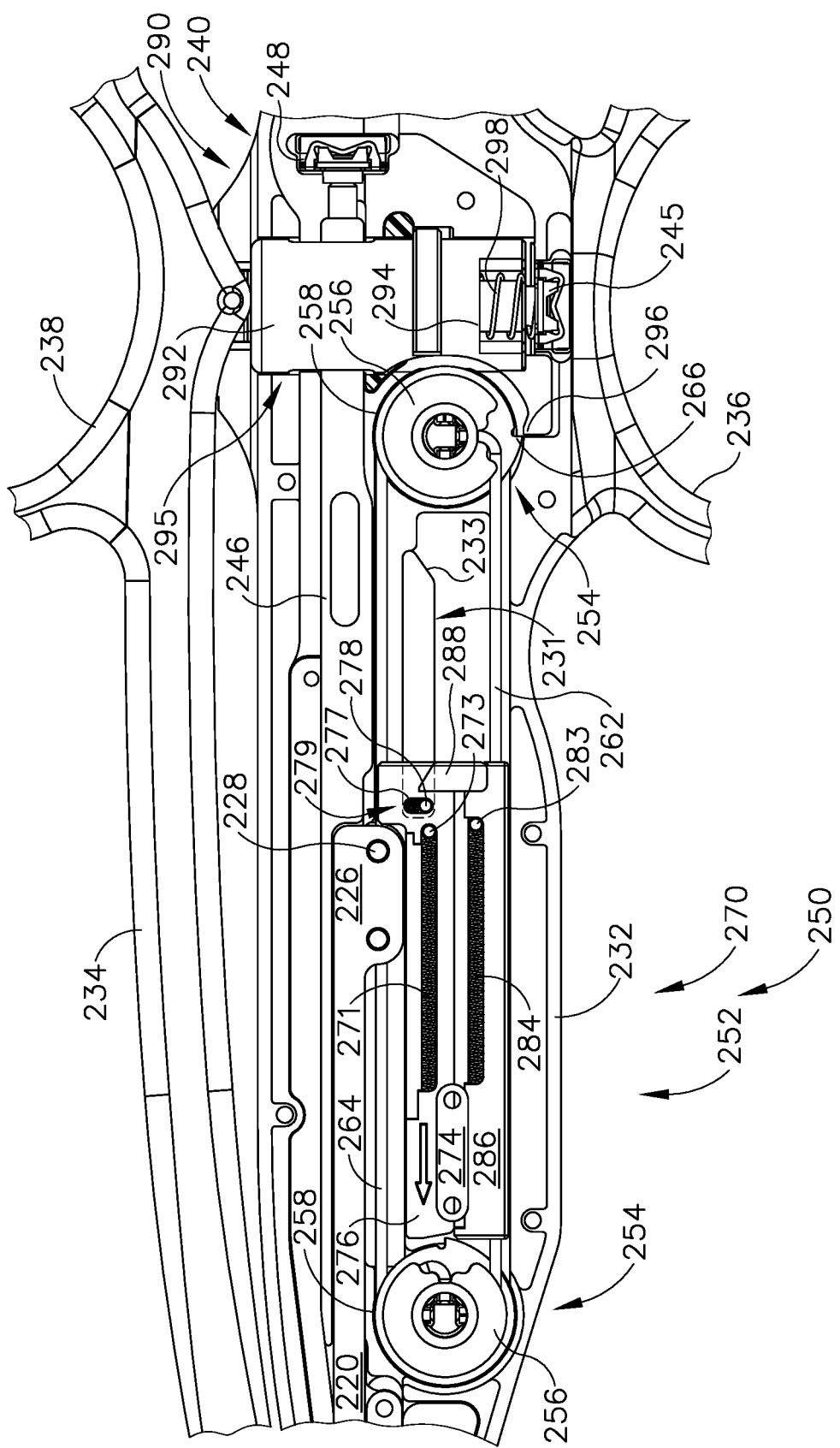
FIG. 15F depicts a side elevational view of a portion of the instrument of FIG. 5, with a portion of the handle assembly of FIG. 7 omitted for clarity, where the end effector is in the closed position, where the resilient arm is in the flexed position, where the lockout assembly of FIG. 8 is in the unlocked configuration, and where the firing assembly of FIG. 9 is returned to the first pre-fired position.

If the operator pulls trigger (251) further in the proximal direction, as shown between FIGS. 15C-15D, transverse driving pin (278) will come into contact with cam surface (233) of slotted pathway (231). Cam surface (233) pushes transverse driving pin (278) upwards within slot (279), overcoming the biasing force of second biasing member (287). Cam surface (233) may push transverse driving pin (288) upwards until pin (278) is no longer engaged with projections (288), as shown in FIG. 15D. With pin (278) no longer engaged with projections (288), biasing member (284) may push against grounding pin (283), therefore actuating second sliding member (280) in the distal direction, as shown in FIG. 15E. Distal actuation of second sliding member (280) causes pulley wheels (254) to rotate in the second angular direction, which causes proximal translation of knife (220). In particular, knife (220) may travel all the way back to the pre-fired position. Once actuated proximally past cam surface (233), biasing member (277) may bias transverse pin (278) back within slot (279).

Projections (288) may also interact with transverse driving pin (278) and second biasing member (277) such that projections (288) may push pin (278) upward out of engagement with projections (288) when knife (220) experiences an excess load, such as when knife (220) encounters an undesirable object. For example, if knife (220) encounters an object difficult to cut, projections (288) may overcome the biasing force of second biasing member (277) such that transverse driving pin (278) actuates upward within slot (279). In other words, if knife (220) encounters an object too difficult to cut, contact between projections (288) and transverse driving pin (278) may generate a force the actuates pin (278) within slot (279) such that pin (278) and projection (288) are no longer in engagement, instead of proximally driving second sliding member (280). Therefore, second sliding member (280) decouples with first sliding member (272) prior to knife (220) reaching the fired position, and knife (220) automatically travels back to the pre-fired position due to first biasing member (284) driving sliding body (286) distally. This may help prevent knife (220) from being damaged.

It should be understood that second sliding member (280) returns to the pre-fired position even though first sliding member (272) is still in the fired position. Therefore, once the operator pulls trigger (251) far enough proximally to complete the distal actuation of knife (220), second sliding member (280) may disengage with first sliding member (272) and automatically return knife (220) to the pre-fired position, regardless if the operator holds trigger (251) in the proximal position. In other words, cam surface (233) of slotted pathway (231), transverse pin (288), and biasing members (184, 187) may act as an automatic knife return mechanism to return knife (220) to the pre-fired poison automatically after reaching a predetermined distal location.

As shown between FIGS. 15E-15F, the operator may release trigger (251) such that biasing member (271) pushes first sliding member (272) back to the position shown in FIG. 15A. The operator may then re-fire knife (220) in accordance with the description herein.

FIGS. 16-18B show an alternative exemplary firing assembly (450) that may be readily incorporated into instrument (200) in replacement of firing assembly (250) described above. Firing assembly (450) includes a rack (470), a rotary drive assembly (452), and an output drive assembly (424). Rack (470) includes an elongate body (472) and a plurality of teeth (474). Rack (470) may be unitarily attached to second sliding member (280) of input drive assembly (270) such that rack (470) may translate with second sliding member (280) in accordance with the description above. As will be described in greater detail below, translation of rack (470) is configured to rotate rotation assembly (452) in order to drive output drive assembly (424).

Output drive assembly (424) includes a proximal body (426) and a cable (428) extending longitudinally along a length of proximal body (426). Proximal body (426) may be used in replacement of proximal body (226) described above. Therefore, proximal body (426) is connected to the proximal end of knife (220) such that translation of proximal body (426) leads to translation of knife (220).

Rotary drive assembly (452) include a pinion (454), a pulley portion (458), and a pin (464). Rotary drive assembly (452) is configured to convert translation of rack (470) in a first direction into translation of output drive assembly (424) in a second, opposite, direction. Pin (464) rotatably couples pinion (454) and pulley portion (458) to housing (232) such that rotary drive assembly (452) may rotate relative to housing (232) about pin (464) but may not translate relative to housing (232).

Pinion (454) and pulley portion (458) rotate together relative to housing (232). Pinion (454) includes a plurality of teeth (456) configured to mesh with teeth (474) of rack (470). Therefore, translation of rack (470) relative to housing (232), in accordance with the description herein, causes rack (470) to drive rotation of pinion (454) and pulley portion (458). Pulley portion (458) includes a first pulley track (460) and a second pulley track (462). Pulley tracks (460, 462) are dimensioned to receive a cable (428) of output drive assembly (424). In particular, cable (428) loops around pulley tracks (460, 462) with sufficient tension such that as pulley portion (458) rotates, cable (428) is fed through tracks (460, 462), thereby actuating proximal body (426).

FIGS. 18A-18B show an exemplary use of alternative firing assembly (450).

FIG. 18A shows firing assembly (450) in a position corresponding to knife (220) being in the pre-fired position. If the operator desires to fire knife (220) from the pre-fired position to the fired position, the operator may suitably grasp tissue in accordance with the teachings herein and pull trigger (251) proximally. Since rack (470) is attached to second sliding member (280), track (470) translates proximally in accordance with the deception herein, as shown in FIG. 18B. Teeth (474) of rack (470) engage teeth (456) of pinion (454), thereby rotating pinion (454) and pulley portion (458) unitarily such that tracks (460, 462) feed along cable (428) and drive proximal body (426) and knife (220) into the fired position. It should be understood that if rack (470) translates from the position shown in FIG. 18B to the position shown in FIG. 18A, in accordance with the teachings herein, knife (220) will translate from the fired position back to the pre-fired position.

While in the current example rack (472) is associated with trigger (251) and cable (428) and proximal body (426) are associated with knife (220) such that trigger (251) actuates rack (472) and proximal body (426) actuates knife (220), this is merely optional. For instance, rack (272) may associate with knife (220); while cable (428) and proximal body (426) may associate with trigger (251) such that trigger (251) actuates proximal body (426) and rack (472) drives knife (220).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) an end effector, wherein the end effector comprises: (i) a first jaw, (ii) a second jaw pivotably coupled with the first jaw, wherein the second jaw is operable to move between an open position and a closed position, (iii) a knife configured to actuate between a pre-fired position and a fired position, and (iv) an electrode assembly configured to apply RF energy to tissue; (b) a handle assembly, wherein the handle assembly comprises: (i) a housing associated with the first jaw, (ii) an arm associated with the second jaw, wherein the arm is configured to pivot the second jaw between the open position and the closed position; and (c) a knife drive assembly comprising: (i) an input assembly, (ii) an output assembly coupled with the knife, and (iii) a compound pulley assembly rotatably disposed within the housing, wherein the compound pulley assembly comprises: (A) a pair of pulley wheels rotatably coupled with the housing, wherein each pulley wheel comprises an input track and an output track, (B) an input cable extending between the input track of each pulley wheel in the pair of pulley wheels, wherein the input cable is fixed to a sliding body of the input assembly, and (C) an output cable extending between the output track of each pulley wheel in the pair of pulley wheels, wherein the output cable is fixed to the output assembly wherein the input assembly is configured to drive the input cable a first proximal distance to in order to rotate the pair of pulley wheels in a first angular direction, thereby driving the output cable a first distal distance to actuate the knife from the pre-fired position toward the fired position.

Example 2

The surgical instrument of Example 1, wherein the first distal distance is greater than the first proximal distance.

Example 3

The surgical instrument of either one or more of Examples 1 through 2, wherein the pair of pulley wheels comprises a proximal pulley wheel and distal pulley wheel, wherein the proximal pulley wheel further comprises an angular lockout projection.

Example 4

The surgical instrument of Example 3, wherein the instrument further comprises a lockout assembly configured to transition between a locked position and an unlocked position, wherein the angular lockout projection is configured to abut again the lockout assembly in the locked position.

Example 5

The surgical instrument of Example 4, wherein the lockout assembly is configured to prevent rotation of the proximal pulley wheel in the locked position.

Example 6

The surgical instrument of Example 5, wherein the arm comprises a resilient member configured to transition between a relaxed position and a flexed position when the jaws are in the closed configuration.

Example 7

The surgical instrument of Example 6, wherein the arm is configured to drive the lockout member from the locked configuration into the unlocked configuration in response to the resilient transitioning from the relaxed position to the flexed position.

Example 8

The surgical instrument of Example 7, wherein the lockout assembly is biased toward the locked position.

Example 9

The surgical instrument of any one or more of Examples 1 through 8, wherein each pulley wheel in the pair of pulley wheels defines a first radial through hole associated with the input track and a second radial through hole associated with the output track, wherein the input cable extends through the first radial through hole, wherein the output cable extends through the second output through hole.

Example 10

The surgical instrument of Example 9, wherein each pulley wheel in the pair of pulley wheels further defines a transverse through hole, wherein the first radial through hole and the second radial through hole both extend into the transverse through hole.

Example 11

The surgical instrument of Example 10, wherein each pulley wheel in the pair of pulley wheels further comprise a core housed within the transverse through hole.

Example 12

The surgical instrument of any one or more of Examples 1 through 11, wherein the input assembly comprises a first sliding member associated with a trigger and a second sliding member associated with the threaded member, where the second sliding member is proximally biased.

Example 13

The surgical instrument of Example 12, wherein the first sliding member is configured to proximally drive the second sliding member to a pre-determined proximal position.

Example 14

The surgical instrument of Example 13, wherein the first sliding member and the second sliding member are configured to disassociate with each other when the second sliding member reaches the pre-determined proximal position.

Example 15

The surgical instrument of any one or more of Examples 1 through 14, wherein the output assembly comprises a coupling block attached to the output cable and a proximal body fixed to the knife, wherein the proximal body is fixed to the coupling block through an interference fit.

Example 16

A surgical instrument comprising: (a) an end effector, wherein the end effector comprises: (i) a first jaw, (ii) a second jaw pivotably coupled with the first jaw, wherein the second jaw is operable to move between an open position and a closed position, (iii) a knife configured to actuate between a pre-fired position and a fired position, and (iv) an electrode assembly configured to apply RF energy to tissue; (b) a handle assembly, wherein the handle assembly comprises: (i) a housing associated with the first jaw, (ii) an arm associated with the second jaw, wherein the arm is pivotably coupled with the housing, wherein the arm is configured to pivot the second jaw between the open configuration and the closed configuration, wherein the arm is configured to transition between a relaxed position and a flexed position while the second jaw is in the closed configuration; and (c) a knife drive assembly comprising: (i) an input assembly, (ii) an output assembly coupled with the knife, and (iii) a pulley, gear, and rack system configured to convert proximal translation of the input assembly into distal translation of the knife and output assembly.

Example 17

The surgical instrument of Example 16, wherein the rack is fixed relative to the output assembly, wherein the input assembly comprises a cable associated with the pulley and the input assembly such that actuation of input assembly causes the cable to rotate the pulley.

Example 18

The surgical instrument of Example 17, wherein proximal actuation of the input assembly is configured to rotate the gear, thereby driving the rack, output assembly, and the knife distally.

Example 19

A surgical instrument comprising: (a) a housing extending distally into a first jaw; (b) an arm pivotably coupled with the housing, wherein the arm extends distally into a second jaw, wherein the arm is operable to drive the second jaw between an open position and a closed position; (c) an electrode assembly associated with the first jaw and the second jaw, wherein the electrode assembly is configured to apply RF energy to tissue; (d) a knife configured to actuate within the first jaw and the second jaw between a pre-fired position and a fired position; (e) a trigger assembly movably coupled with the housing, and (f) a knife actuation assembly configured to actuate the knife between the pre-fired position and the fired position, wherein the knife actuation assembly comprises: (i) a pulley and cable system comprising an input cable and an output cable, (ii) an output body coupled with the output cable and the knife, and (iii) an input body coupled with the input cable, wherein the trigger assembly is configured to drive the input body proximally such that the pulley and cable system drives the knife from the pre-fired position to the fired position, wherein the input body and trigger assembly are configured to decouple from each other when the input body reaches a pre-determined proximal position.

Example 20

The surgical instrument of Example 19, wherein the input member is biased to a position corresponding to the knife being in the pre-fired position.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. App. Ser. No. 15/989,424, entitled "Method and Apparatus for Open Electrosurgical Shears," filed on May 25, 2018, published as U.S. Pub. No. 2019/0357962 on Nov. 28, 2019, issued as U.S. Pat. No. 11,020,169 on Jun. 1, 2021; U.S. App. Ser. No. 15/989,430, entitled "Electrosurgical Shears with Knife Lock and Clamp-Actuated Switch," filed on May 25, 2018, published as U.S. Pub. No. 2019/0357969 on Nov. 28, 2019, issued as U.S. Pat. No. 10,966,781 on Apr. 6, 2021; U.S. App. Ser. No. 15/989,433, entitled "Knife Drive Assembly for Electrosurgical Shears," filed on May 25, 2018, published as U.S. Pub. No. 2019/0357963 on Nov. 28, 2019, issued as U.S. Pat. No. 11,020,170 on Jun. 1, 2021; U.S.

App. Ser. No. 15/989,438, entitled "Knife Auto-Return Assembly for Electrosurgical Shears," filed on May 25, 2018, issued as U.S. Pat. No. 10,898,259 on Jan. 26, 2021; U.S. App. Ser. No. 15/989,422, entitled "Compound Screw Knife Drive for Electrosurgical Shears," filed on May 25, 2018, issued as U.S. Pat. No. 10,856,931 on Dec. 8, 2020; U.S. App. Ser. No. 15/989,452, entitled "Dual Stage Energy Activation for Electrosurgical Shears," filed on May 25, 2018, published as U.S. Pub. No. 2019/0357967 on Nov. 28, 2019; and U.S. App. Ser. No. 15/989,455, entitled "Latching Clamp Arm for Electrosurgical Shears," filed on May 25, 2018, published as U.S. Pub. No. 2019/0357968 on Nov. 28, 2019, issued as U.S. Pat. No. 11,039,877 on Jun. 22, 2021. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:
1. A surgical instrument comprising:
 (a) an end effector, wherein the end effector comprises:
  (i) a first jaw,
  (ii) a second jaw pivotably coupled with the first jaw, wherein the second jaw is operable to move between an open position and a closed position,
  (iii) a knife configured to actuate between a pre-fired position and a fired position, and
  (iv) an electrode assembly configured to apply RF energy to tissue;
 (b) a handle assembly, wherein the handle assembly comprises:
  (i) a housing associated with the first jaw,
  (ii) an arm associated with the second jaw, wherein the arm is configured to pivot the second jaw between the open position and the closed position; and
 (c) a knife drive assembly comprising:
  (i) an input assembly,
  (ii) an output assembly coupled with the knife, and
  (iii) a compound pulley assembly rotatably disposed within the housing, wherein the compound pulley assembly comprises:
   (A) a pair of pulley wheels rotatably coupled with the housing, wherein each pulley wheel comprises an input track and an output track,
   (B) an input cable extending between the input track of each pulley wheel in the pair of pulley wheels, wherein the input cable is fixed to a sliding body of the input assembly, and
   (C) an output cable extending between the output track of each pulley wheel in the pair of pulley wheels, wherein the output cable is fixed to the output assembly,
  wherein the input assembly is configured to drive the input cable a first proximal distance to in order to rotate the pair of pulley wheels in a first angular direction, thereby driving the output cable a first distal distance to actuate the knife from the pre-fired position toward the fired position, wherein the first distal distance is greater than the first proximal distance.

2. The surgical instrument of claim 1, wherein the pair of pulley wheels comprises a proximal pulley wheel and distal pulley wheel, wherein the proximal pulley wheel further comprises an angular lockout projection.

3. The surgical instrument of claim 2, wherein the surgical instrument further comprises a lockout assembly configured to transition between a locked position and an unlocked position, wherein the angular lockout projection is configured to abut again the lockout assembly in the locked position.

4. The surgical instrument of claim 3, wherein the lockout assembly is configured to prevent rotation of the proximal pulley wheel in the locked position.

5. The surgical instrument of claim 4, wherein the arm comprises a resilient member configured to transition between a relaxed position and a flexed position when the second jaw is in the closed position.

6. The surgical instrument of claim 5, wherein the arm is configured to drive the lockout assembly from the locked position into the unlocked position in response to the resilient transitioning from the relaxed position to the flexed position.

7. The surgical instrument of claim 6, wherein the lockout assembly is biased toward the locked position.

8. The surgical instrument of claim 1, wherein each pulley wheel in the pair of pulley wheels defines a first radial through hole associated with the input track and a second radial through hole associated with the output track, wherein the input cable extends through the first radial through hole, wherein the output cable extends through the second radial through hole.

9. The surgical instrument of claim 8, wherein each pulley wheel in the pair of pulley wheels further defines a transverse through hole, wherein the first radial through hole and the second radial through hole both extend into the transverse through hole.

10. The surgical instrument of claim 9, wherein each pulley wheel in the pair of pulley wheels further comprise a core housed within the transverse through hole.

11. The surgical instrument of claim 1, wherein the input assembly comprises a first sliding member associated with a trigger and a second sliding member associated with the input cable, where the second sliding member is proximally biased.

12. The surgical instrument of claim 11, wherein the first sliding member is configured to proximally drive the second sliding member to a pre-determined proximal position.

13. The surgical instrument of claim 12, wherein the first sliding member and the second sliding member are configured to disassociate with each other when the second sliding member reaches the pre-determined proximal position.

14. The surgical instrument of claim 1, wherein the output assembly comprises a coupling block attached to the output cable and a proximal body fixed to the knife, wherein the proximal body is fixed to the coupling block through an interference fit.

15. The surgical instrument of claim 1, wherein the knife comprises a distal cutting edge.

16. A surgical instrument comprising:
 (a) an end effector, wherein the end effector comprises:
  (i) a first jaw,
  (ii) a second jaw pivotably coupled with the first jaw, wherein the second jaw is operable to move between an open position and a closed position,
  (iii) a knife configured to actuate between a pre-fired position and a fired position, and
  (iv) an electrode assembly configured to apply RF energy to tissue;
 (b) a handle assembly, wherein the handle assembly comprises:
  (i) a housing associated with the first jaw, and
  (ii) an arm associated with the second jaw, wherein the arm is pivotably coupled with the housing, wherein the arm is configured to pivot the second jaw between the open position and the closed position, wherein the arm is configured to transition between a relaxed position and a flexed position while the second jaw is in the closed position; and
 (c) a knife drive assembly comprising:
  (i) an input assembly,
  (ii) an output assembly coupled with the knife,
  (iii) a pulley, gear, and rack system configured to convert proximal translation of the input assembly into distal translation of the knife and output assembly, and
  (iv) a cable associated with either the input assembly or the output assembly, wherein the cable is configured to translate, in its entirety, with the input assembly or the output assembly associated with the cable.

17. The surgical instrument of claim 16, wherein the rack is fixed relative to the output assembly, wherein the input assembly comprises the cable, wherein the cable is associated with the pulley such that actuation of input assembly causes the cable to rotate the pulley.

18. The surgical instrument of claim 17, wherein proximal actuation of the input assembly is configured to rotate the gear, thereby driving the rack, the output assembly, and the knife distally.

19. A surgical instrument comprising:
 (a) a housing extending distally into a first jaw;
 (b) an arm pivotably coupled with the housing, wherein the arm extends distally into a second jaw, wherein the arm is operable to drive the second jaw between an open position and a closed position;
 (c) an electrode assembly associated with the first jaw and the second jaw, wherein the electrode assembly is configured to apply RF energy to tissue;
 (d) a knife configured to actuate within the first jaw and the second jaw between a pre-fired position and a fired position;
 (e) a trigger assembly movably coupled with the housing, and
 (f) a knife actuation assembly configured to actuate the knife between the pre-fired position and the fired position, wherein the knife actuation assembly comprises:
  (i) a pulley and cable system comprising an input cable and an output cable,
  (ii) an output body coupled with the output cable and the knife, and
  (iii) an input body coupled with the input cable, wherein the trigger assembly is configured to drive the input body proximally such that the pulley and cable system drives the knife from the pre-fired position to the fired position, wherein the input body and trigger assembly are configured to decouple from each other when the input body reaches a pre-determined proximal position.

20. The surgical instrument of claim 19, wherein the input body is biased to a position corresponding to the knife being in the pre-fired position.

* * * * *